(12) United States Patent
Li et al.

(10) Patent No.: US 12,011,439 B2
(45) Date of Patent: Jun. 18, 2024

(54) COMBINATION THERAPY USING C—C CHEMOKINE RECEPTOR 4 (CCR4) ANTAGONISTS AND ONE OR MORE IMMUNE CHECKPOINT INHIBITORS

(71) Applicant: CHEMOCENTRYX, INC., San Carlos, CA (US)

(72) Inventors: Shijie Li, Los Altos, CA (US); Venkat Reddy Mali, Cupertino, CA (US); Rajinder Singh, Belmont, CA (US); Ju Yang, Palo Alto, CA (US); Penglie Zhang, Foster City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

(21) Appl. No.: 17/820,179

(22) Filed: Aug. 16, 2022

(65) Prior Publication Data
US 2023/0097128 A1     Mar. 30, 2023

Related U.S. Application Data

(63) Continuation of application No. 16/553,339, filed on Aug. 28, 2019, now Pat. No. 11,446,289.

(60) Provisional application No. 62/771,853, filed on Nov. 27, 2018, provisional application No. 62/724,412, filed on Aug. 29, 2018.

(51) Int. Cl.
| *A61K 31/4545* | (2006.01) |
| *A61K 31/165* | (2006.01) |
| *A61K 31/357* | (2006.01) |
| *A61K 39/395* | (2006.01) |
| *A61P 35/00* | (2006.01) |

(52) U.S. Cl.
CPC ........ *A61K 31/4545* (2013.01); *A61K 31/165* (2013.01); *A61K 31/357* (2013.01); *A61K 39/39541* (2013.01); *A61P 35/00* (2018.01)

(58) Field of Classification Search
CPC .............. A61K 31/4545; A61K 31/165; A61K 31/357; A61K 39/39541; A61K 45/06; A61K 2039/505; A61K 2039/82; A61K 2039/852; A61K 2300/00; A61P 35/00; C07K 16/2818
See application file for complete search history.

(56) References Cited

U.S. PATENT DOCUMENTS

| 8,835,419 | B2 * | 9/2014 | Charvat | C07D 401/04 |
| | | | | 514/254.01 |
| 9,567,323 | B2 * | 2/2017 | Charvat | A61K 31/451 |
| 9,758,512 | B2 * | 9/2017 | Charvat | C07D 417/04 |
| 10,407,417 | B2 | 8/2019 | Charvat et al. | |
| 11,142,521 | B2 * | 10/2021 | Charvat | A61P 9/00 |
| 11,446,289 | B2 * | 9/2022 | Li | A61K 45/06 |
| 2011/0009842 | A1 | 1/2011 | Minato et al. | |
| 2012/0214955 | A1 | 8/2012 | Ren et al. | |
| 2012/0214957 | A1 | 8/2012 | Li et al. | |
| 2012/0226005 | A1 | 9/2012 | Yao et al. | |
| 2012/0232236 | A1 | 9/2012 | Li et al. | |
| 2016/0317545 | A1 * | 11/2016 | Charvat | A61K 31/451 |
| 2018/0072740 | A1 | 3/2018 | Beck et al. | |
| 2022/0194929 | A1 | 6/2022 | Charvat et al. | |

FOREIGN PATENT DOCUMENTS

| JP | 2007-210887 A | 8/2007 |
| WO | 2004/010943 A2 | 2/2004 |
| WO | 2007/063934 A1 | 6/2007 |
| WO | 2009/037454 A2 | 3/2009 |
| WO | 2009/100140 A1 | 8/2009 |
| WO | 2012/080729 A2 | 6/2012 |
| WO | 2013/082490 A1 | 6/2013 |
| WO | 2017/194265 A1 | 11/2017 |
| WO | 2018/005374 A1 | 1/2018 |
| WO | 2018/035710 A1 | 3/2018 |
| WO | 2018/101448 A1 | 6/2018 |

OTHER PUBLICATIONS

Tanaka, et al., Cell Research 2017 vol 27 pp. 109-118 (Year: 2017).*
Ishida, et al., Cancer Sci 2006, vol. 97, No. 11 pp. 1139-1146 (Year: 2006).*
Nyu, et al., Clinical Trial NCT02868632; First Posted Aug. 16, 2016 (Year: 2016).*
Agenus, et al., Clinical Trial NCT02694822; First Published Mar. 1, 2016 (Year: 2016).*
Agenus, et al., Press Release Jul. 28, 2016 (Year: 2016).*
International Search Report and Written Opinion corresponding to PCT/US2012/067385, dated Apr. 3, 2013; 6 pages.
International Search Report dated Nov. 4, 2019 corresponding to PCT/US2019/048461 filed Aug. 28, 2019; 19 pages.
Extended European Search Report dated Apr. 25, 2022 corresponding to EP 19854176.5 filed Aug. 28, 2019; 9 pages.
Dermer, Gerald B.; "Another Anniversary for the War on Cancer," *Bio/Technology* (Mar. 1994) 12:320.
Freshney, R. Ian; *Culture of Animal Cells, A Manual of Basic Technique*; Alan R. Liss, Inc. (© 1983, New York, NY; 4 pages.
Gura, Trisha; Systems for Identifying New Drugs are Often Faulty; *Science*; (Nov. 7, 1997); 278:1041-1042.
Guzik, Katarzyna et al., "Small-Molecule Inhibitors of the Programmed Cell Death-1/Programmed Death-Ligand 1 (PD-1/PD-L1) Interaction via Transiently Induced Protein States and Dimerization of PD-L1," *J. Med. Chem.* (Jun. 14, 2017) 60:5857-5867.

(Continued)

*Primary Examiner* — Julie Wu
*Assistant Examiner* — John L Van Druff
(74) *Attorney, Agent, or Firm* — Robert Bernstein

(57) ABSTRACT

The present disclosure is drawn to the combination therapy of a C-C Chemokine Receptor 4 (CCR4) antagonist and one or more immune checkpoint inhibitors in the treatment of cancer.

10 Claims, 11 Drawing Sheets

(56) References Cited

OTHER PUBLICATIONS

Solori, Roberto et al., "Targeting chemokine receptors in disease—a case study of CCR4," *European Journal of Pharmacology* (Accepted May 12, 2015); 763:169-177.
Sato, T. et al., "Internalization of CCR4 and inhibition of chemotaxis by K777, a potent and selective CCR4 antagonist," *Pharmacology* (2013; Epub Jun. 5, 2013) 91(5-6):305-313; abstract only.
Ishida, Takashi et al., "CCR4 as a novel molecular target for immunotherapy of cancer," Cancer Sci., Nov. 2006, vol. 97(11), pp. 1139-1146.
Kyowa Kirin ClinicalTrials.gov Identifier: NCT02301130; First posted Nov. 25, 2014; 8 pages.
Tanaka, Atsushi et al., "Regulatory T cells in cancer immunotherapy," *Cell Research* (2017; published online Dec. 20, 2016) 27:109-118.
Wu et al., "Cell-based optimization of novel benzamides as potential antimalarial leads," Bioorganic & Medicinal Chemistry Letters 19, 2009, pp. 6970-6974.
Zamarin, Dmitriy et al., Mogamulizumab in Combination with Durvalumab or Tremelimumab in Patients with Advanced Solid Tumors: a Phase I Study, *Clin Cancer Res*. (Sep. 1, 2020) 26(17):4531-4541.

\* cited by examiner

Previous treatment: a-CTLA-4/Compound 1

Re-challenge With CT26:

Previous treatment: a-CTLA-4/Compound 1

First challenge With 4T1:

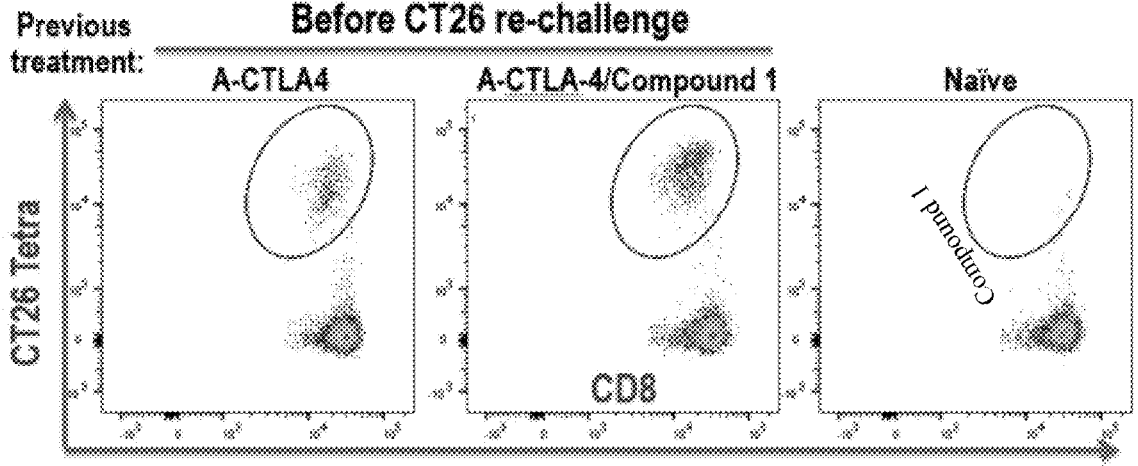
FIG. 9A
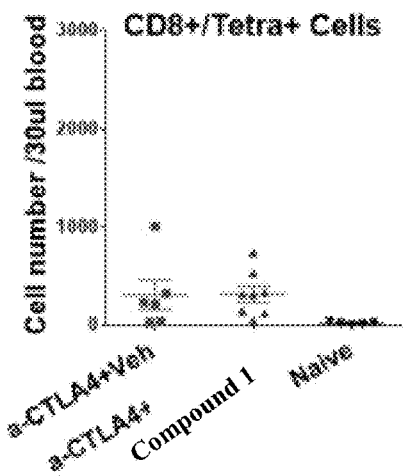
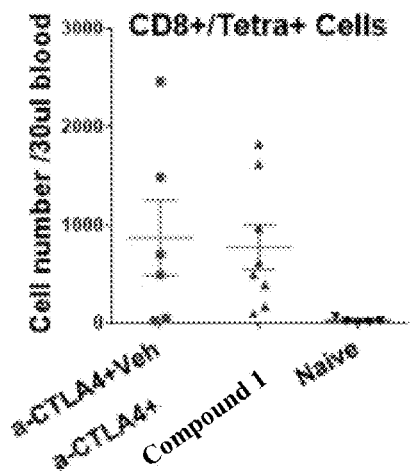
FIG. 9B    FIG. 9C

COMBINATION THERAPY USING C—C CHEMOKINE RECEPTOR 4 (CCR4) ANTAGONISTS AND ONE OR MORE IMMUNE CHECKPOINT INHIBITORS

CROSS-REFERENCES TO RELATED APPLICATIONS

This application is a continuation of U.S. patent application Ser. No. 16/553,339 filed Aug. 28, 2019, which is an application claiming the benefit of priority under 35 U.S.C § 119(e) to U.S. Provisional Application Ser. No. 62/724,412 filed Aug. 29, 2018 and 62/771,853 filed Nov. 27, 2018, the disclosure of each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

Cancer is a class of diseases in which a group of cells display dysregulated replication and growth. Recent cancer models implicate the immune system, including cellular homing and immune checkpoints, in cancer development and progression. Although great progress has been made in understanding the biological basis of cancer, this disease remains a leading cause of death.

The CC Chemokine receptor 4, CCR(4), first identified by Power et al. (Power et al. (1995) *J. Biol. Chem.* 270:19495-19500), is a G protein-coupled receptor that binds to chemokines including CCL22, also known as Macrophage-Derived Chemokine (MDC; a CC chemokine reported to be a chemoattractant for the Th2 subset of peripheral blood T cells, dendritic cells, and natural killer (NK) cells), and CCL17, also known as TARC (thymus and activation-regulated chemokine), which is also produced by monocytes and dendritic cells.

CCR(4) is involved in immuoregulatory processes such as the homing of cells to specific tissues including T lymphocyte homing to the skin and lungs (see, e.g., Campbell et al. (1999) *Nature* 400:776-780, Gonzalo et al. (1999) *J. Immunol.* 163:403-5 411, Lloyd et al. (2000) *J. Exp. Med.* 191:265-273, Kawasaki et al. (2001) *J. Immunol.* 166:2055-2062). Modulators of CCR4 activity have been described in, for example, WO 2013/082490.

Cytotoxic T lymphocyte antigen-4 (CTLA-4) is believed to be a key regulator of the adaptive immune responses. In particular, CLTA-4 is understood to play a central role in the maintenance of and repertoire of emergent T cell responses. As such, CTLA-4 is recognized as a possible therapeutic target for the treatment of cancer and inflammation as an immune checkpoint inhibitor. CLTA-4 modulatorys have been described in, for example, WO 2018/035710.

Programmed death-1 (PD-1) is a transmembrane receptor protein that negatively regulates the function of T cells through interaction with its two native ligands PD-L1 and PD-L2. Like CTLA4, PD-1 is also a central regulator of the immune system, and is also considered an immune checkpoint inhibitor. PD-1/PD-L1 modulators have been described in, for example, WO 2018/005374.

Given the role of cellular homing and immune checkpoint pathways in cancer development and progression, the need exists for developing combination therapies that can improve cancer treatment.

BRIEF SUMMARY

The present disclosure is drawn to the combination therapy of a C-C Chemokine Receptor 4 (CCR4) antagonist and one or more checkpoint inhibitors in the treatment of cancer.

In some embodiments, the CCR4 receptor antagonist has the Formula I

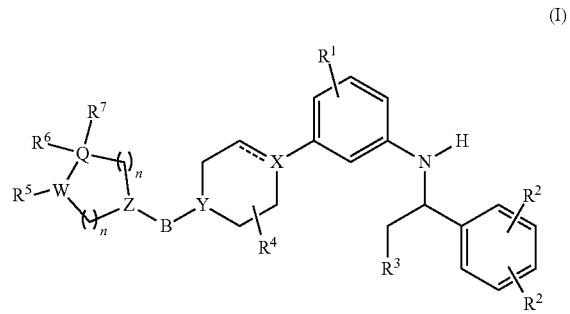

(I)

where each variable is described below.

In some embodiments, the CCR4 antagonist has the formula

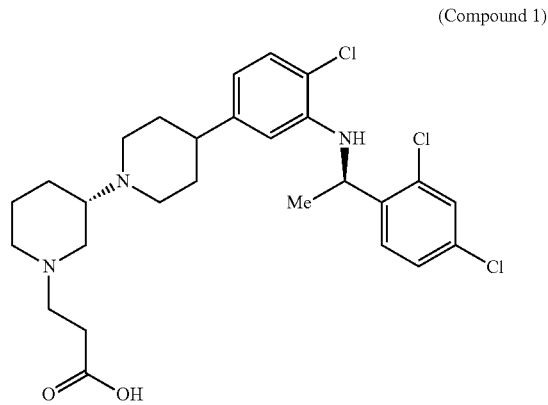 [SMILES: C[C@@H](Nc1cc(C2CCN([C@H]3CCCN(CCC(=O)O)C3)CC2)ccc1Cl)c1ccc(Cl)cc1Cl]

(Compound 1)

or a pharmaceutically acceptable salt thereof.

In some embodiments, the CCR4 antagonist has the formula

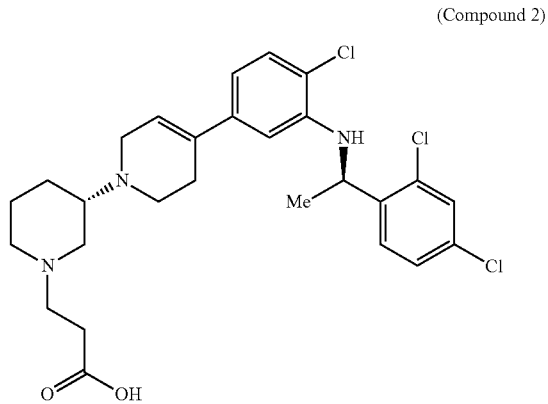 [SMILES: C[C@@H](Nc1cc(C2=CCN([C@H]3CCCN(CCC(=O)O)C3)CC2)ccc1Cl)c1ccc(Cl)cc1Cl]

(Compound 2)

or a pharmaceutically acceptable salt thereof.

In some embodiments, the CCR4 antagonist has the formula

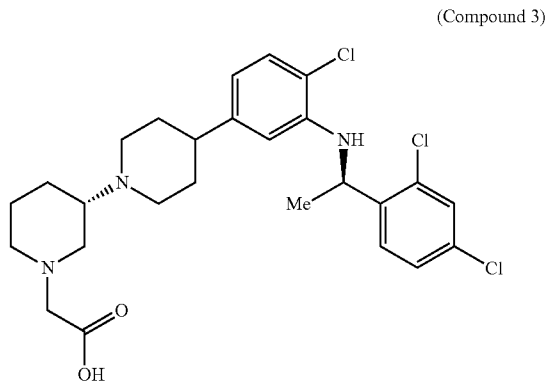 [SMILES: C[C@@H](Nc1cc(C2CCN([C@H]3CCCN(CC(=O)O)C3)CC2)ccc1Cl)c1ccc(Cl)cc1Cl]

(Compound 3)

or a pharmaceutically acceptable salt thereof.

In some embodiments, the CCR4 antagonist has the formula

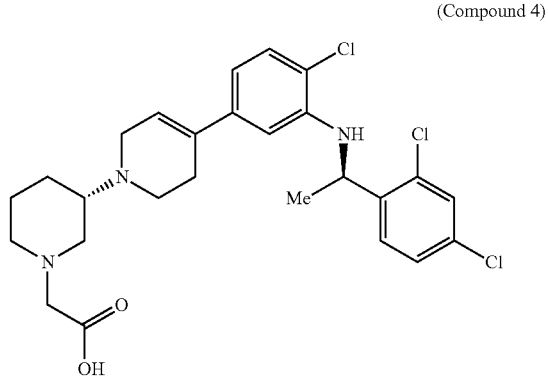 [SMILES: C[C@@H](Nc1cc(C2=CCN([C@H]3CCCN(CC(=O)O)C3)CC2)ccc1Cl)c1ccc(Cl)cc1Cl]

(Compound 4)

or a pharmaceutically acceptable salt thereof.

BRIEF DESCRIPTION OF THE DRAWINGS

FIG. 9A-C plots flow cytometry results from blood samples obtained from the mice tested in FIG. 8. Panel A shows that before re-challenge mice previously exposed to CT26 cells (and treated CTLA-4 or anti-CTLA-4 and Compound 1) have cytotoxic T cells against CT26 tumor cells, while naïve mice do not. Panels B and C show the number of cytotoxic T cells responsive against CT26 tumor cells before re-challenge and 1 week after re-challenge.

DETAILED DESCRIPTION

I. General

Figure 1:
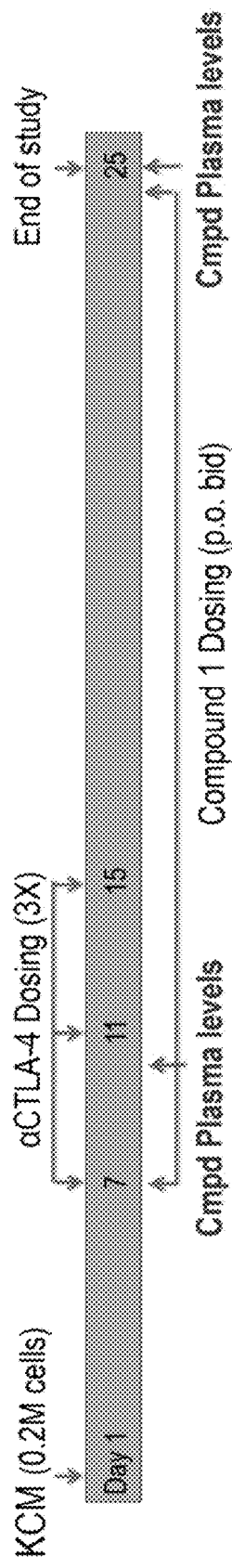
FIG. 1 illustrates the study design used for the KCM Orthotopic pancreatic tumor model.
Figure 2C:
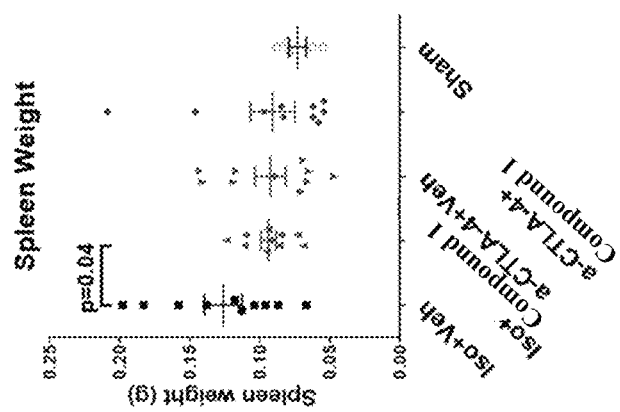
FIG. 2A-C displays the primary tumor+pancreas weight (Panel A), the total tumor+Pancreas weight (Panel B), and the spleen weight (Panel C) of each cohort tested. Combination therapy of an anti-CTLA-4 antibody and Compound 1 reduced tumor weight as compared to antibody or Compound 1 alone.
Figure 2B:
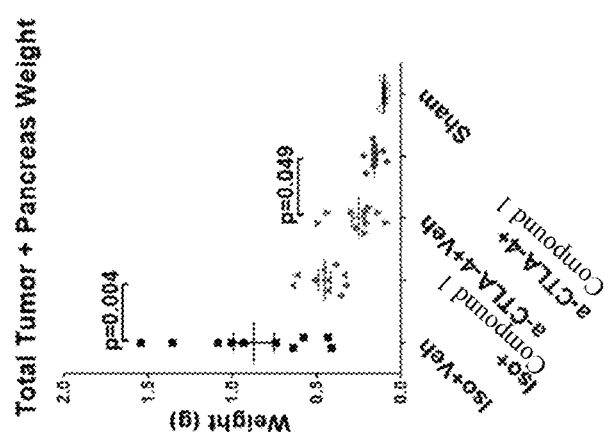
Figure 2A:
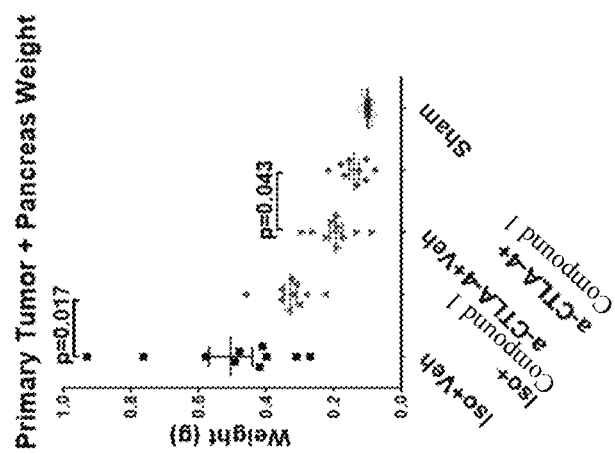
Figures 3A, 3B, 3C:
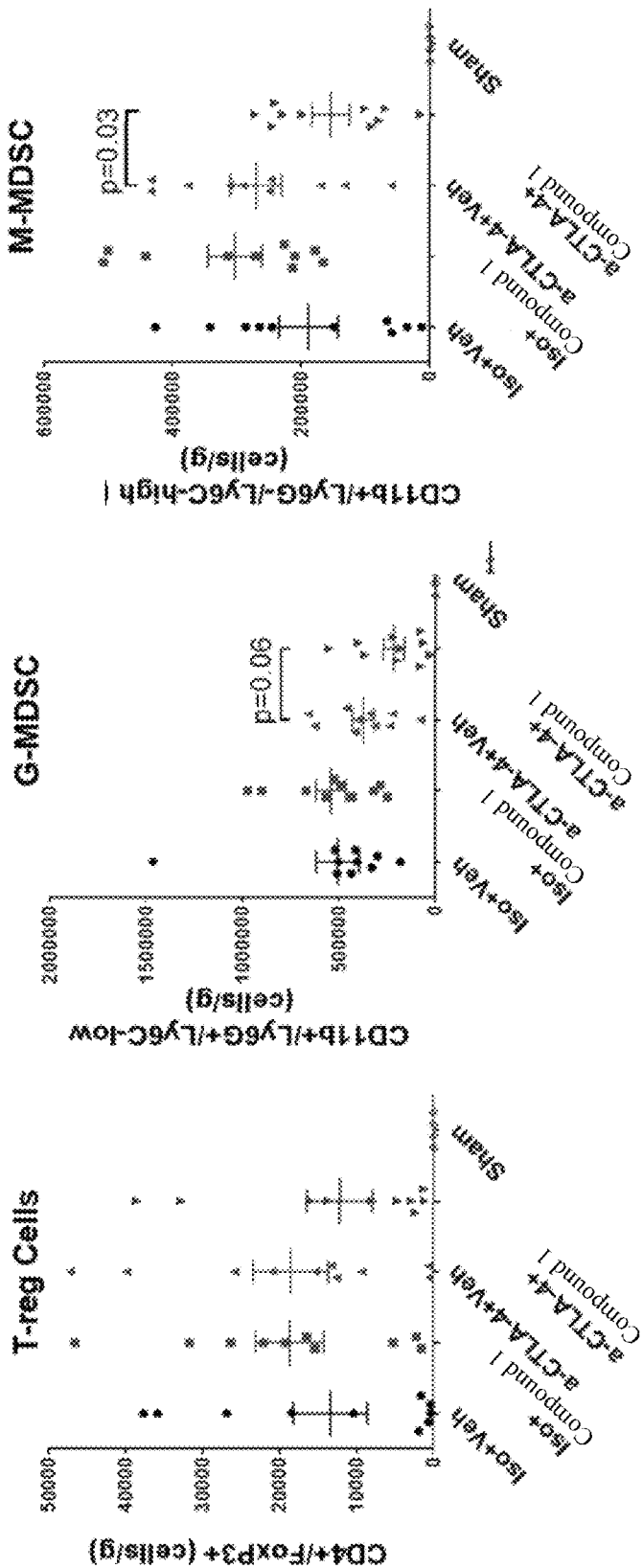
FIG. 3A-F reports the relative amounts of suppressive immune cell populations in each cohort tested. Panels A-C report the cells per gram of tissue, while Panels D-F report the percent of CD45+ cells. Panels A & D report T-reg cells; panels B & E report G-MDSC cells; and panels C & F report M-MDSC cells.
Figure 3F:
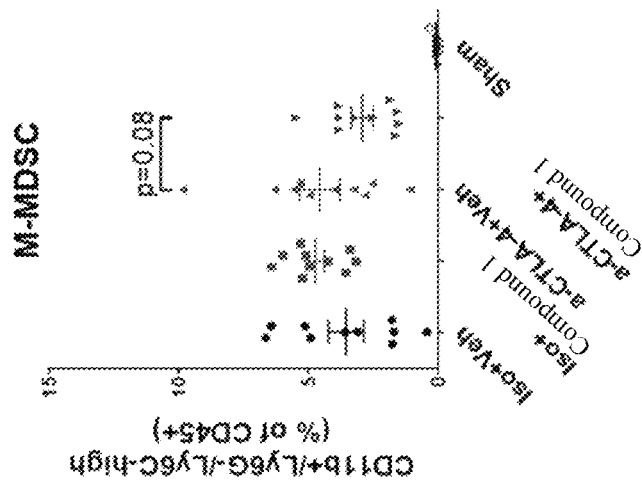
Figure 3E:
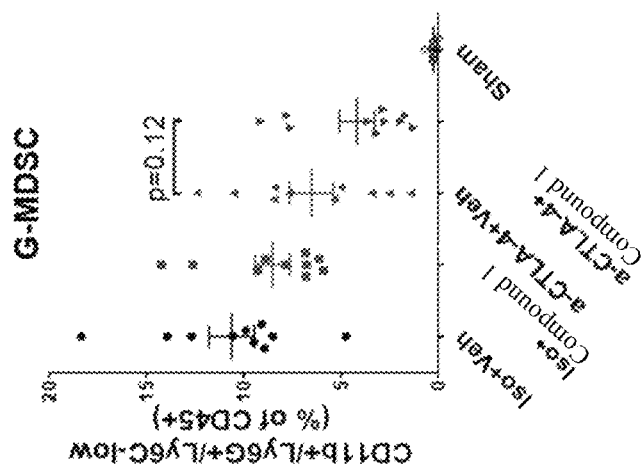
Figure 3D:
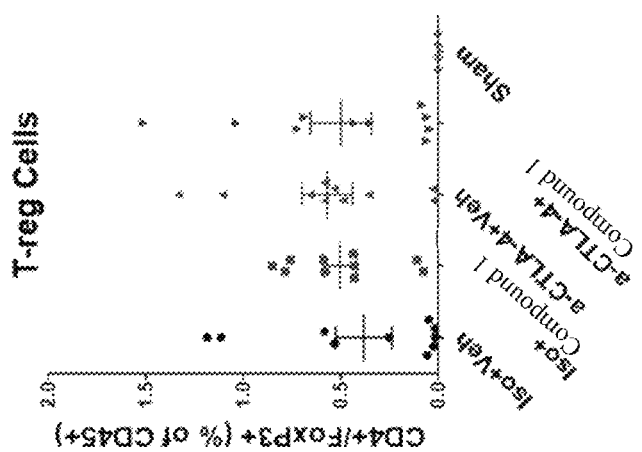

The present disclosure is drawn to the surprising and unexpected finding that combination therapy using a CCR4 antagonist and one or more immune checkpoint inhibitor significantly improves cancer treatment as compared to the one or more checkpoint inhibitors on their own.

II. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom. For terms such as cycloalkylalkyl and heterocycloalkylalkyl, it is meant that a cycloalkyl or a heterocycloalkyl group is attached through an alkyl or alkylene linker to the remainder of the molecule. For example, cyclobutylmethyl—is a cyclobutyl ring that is attached to a methylene linker to the remainder of the molecule.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group that is attached to the remainder of the molecule (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR' R", —C(O)R', —OC(O)NR' R", —NR"C(O)R', —NR"C(O)$_2$R'—NR'—C(O)NR"R'", —NH—C(NH$_2$)=NH, —NR' C(NH$_2$)=NH, —NH—C (NH$_2$)=NR', —S(O)R', —S(O)$_2$R', —S(O)$_2$NR'R", —NR'S (O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

For the compounds provided herein, a bond that is drawn from a substituent (typically an R group) to the center of an aromatic ring (e.g., benzene, pyridine, and the like) will be understood to refer to a bond providing a connection at any of the available vertices of the aromatic ring. In some embodiments, the depiction will also include connection at a ring which is fused to the aromatic ring. For example, a bond drawn to the center of the benzene portion of an indole, will indicate a bond to any available vertex of the six- or five-membered ring portions of the indole.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When compounds are provided herein with an identified stereochemistry (indicated as R or S, or with dashed or wedge bond designations), those compounds will be understood by one of skill in the art to be substantially free of other isomers (e.g., at least 80%, 90%, 95%, 98%, 99%, and up to 100% free of the other isomer).

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

As used herein, the term "selective CCR4 antagonist" refers to a highly discriminatory compound that inhibits CCR4 activity with little or no cross reactivity on non-targeted proteins such as CCR1, CCR2, CCR3, CCR5, CCR6, CCR7, CCR8, CCR9, CCR10, CCR12, CXCR1, CXCR2, CXCR3, CXCR4, CXCR5, CXCR6, and/or CXCR7. In some embodiments, "selective CCR4 antagonists" have an $IC_{50}$ that is at least 10; 100; 500; 1,000; 2,000; 5,000; or more times lower than for that of proteins such as CCR1, CCR2, CCR3, CCR5, CCR6, CCR7, CCR8, CCR9, CCR10, CCR12, CXCR1, CXCR2, CXCR3, CXCR4, CXCR5, CXCR6, and/or CXCR7 when measured in the assays used in Example 3 of this application. In some embodiments, "selective CCR4 antagonists" do not inhibit the activity of CCR1, CCR2, CCR3, CCR5, CCR6, CCR7, CCR8, CCR9, CCR10, CCR12, CXCR1, CXCR2, CXCR3, CXCR4, CXCR5, CXCR6, and/or CXCR7 at concentrations of 1 μM or below in assays used in Example 2 of this application. The above-mentioned proteins are considered to be "not inhibited" when they maintain 100%, 99%, 95%, 90%, or 85% of their activity under the referenced conditions with a selective CCR4 antagonist.

III. Combination Therapy Using CCR4 Antagonists and One or More Immune Checkpoint Inhibitors Provided herein are methods, compositions, and kits that take advantage of the synergistic effect of CCR4 antagonists and immune checkpoint inhibitors in treating cancer. A combination treatment that includes both a CCR4 antagonist and one or more immune checkpoint inhibitors is more effective at treating cancer compared to each treatment on its own.

Cancer generally includes any of various malignant neoplasms characterized by the proliferation of anaplastic cells that tend to invade surrounding tissue and metastasize to new body sites. Non-limiting examples of different types of cancer suitable for treatment using the compositions of the present disclosure include ovarian cancer, breast cancer, lung cancer (such as non-small-cell lung carcinoma), bladder cancer, thyroid cancer, liver cancer, pleural cancer, pancreatic cancer, cervical cancer, prostate cancer, testicular cancer, colon cancer, anal cancer, colorectal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

In some embodiments, the cancer is lung cancer (e.g., non-small-cell lung carcinoma), melanoma, an epithelial cancer (e.g., prostate cancer, ovarian cancer, breast cancer), or a blood cancer (e.g., leukemia, lymphoma, multiple myeloma).

In some embodiments, the cancer is a solid cancer. In some embodiments, the cancer is pancreatic cancer. In some embodiments, the cancer is colon cancer.

A. CCR4 Antagonists

CCR4 antagonists are compounds that reduce or inhibit CCR4 activity. There are a number of such compounds known in the art. In some embodiments, the CCR4 antagonists of the present disclosure are selective CCR4 antagonists.

In some embodiments, the CCR4 antagonists is a small molecule inhibitor of CCR4 having the Formula (I):

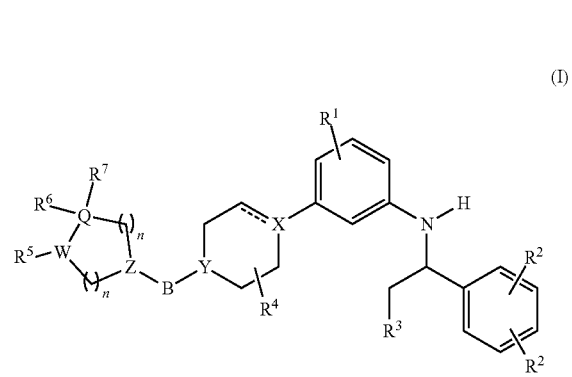

(I)

and a pharmaceutically acceptable salt thereof, wherein $R^1$ is selected from hydrogen, $C_{1-8}$ alkyl, $C_{1-8}$ haloalkyl, $C_{1-8}$ hydroxyalkyl, $C_{3-8}$ cycloalkyl, halogen, —CN, —SO$_2$Me and —C(O)NH$_2$;

each $R^2$ is selected from $C_{1-8}$ alkyl, $C_{1-8}$haloalkyl, halogen, —CN and $C_{1-8}$ alkoxy; or two $R^2$ groups attached to adjacent carbon atoms are optionally connected to form a 5 or 6 member ring (aliphatic or aromatic, cycloalkyl or heterocycloalkyl);

$R^3$ is selected from hydrogen, methyl and $C_{1-4}$haloalkyl;

$R^4$ is selected from hydrogen, $C_{1-8}$ alkyl, $C_{1-8}$ haloalkyl and $C_{1-8}$ hydroxyalkyl;

each of the subscripts n is independently an integer from 0 to 3;

B is a bond or C(O);

Q is a selected from C, CH, N, O, S, S(O), and SO$_2$;

W, X, Y, and Z are independently selected from C, CH and N, but Q and W are not both N;

$R^5$ and $R^6$ are absent or are independently selected from H, —OH, $C_{1-8}$ alkyl, $C_{1-8}$ hydroxyalkyl, $C_{1-4}$ alkoxy-$C_{1-4}$ alkyl, —C(O)NR$^a$R$^b$, $C_{1-8}$ alkylene-C(O)NR$^a$R$^b$, —NH—$C_{1-4}$alkylene-C(O)NR$^a$R$^b$, —C(O)—$C_{1-4}$ alkylene-NR$^a$R$^b$, —CO$_2$H and acid isosteres, $C_{1-8}$ alkylene-CO$_2$H and acid isosteres, —N(R$^a$)C(O) NR$^a$R$^b$, $C_{1-8}$ alkylene-N(R$^a$)C(O)NR$^a$R$^b$, —NR$^a$R$^b$, $C_{1-8}$ alkylene-NR$^a$R$^b$, $C_{1-8}$ alkoxy, —C(O)OR$^a$, $C_{1-8}$ alkylene-C(O)OR$^a$, —CN, —C(O)R$^a$, —SO$_2$R$^a$ and —N(R$^a$)C(O)R$^b$;

wherein each R$^a$ and R$^b$ are independently selected from hydrogen, $C_{1-8}$ alkyl, $C_{1-8}$ hydroxyalkyl, $C_{1-8}$ haloalkyl, and $C_{1-8}$ alkoxy; and $R^7$ is absent or is selected from H, $C_{1-8}$ alkyl and $C_{1-8}$ haloalkyl.

In one group of embodiments, the compounds provided herein are those wherein X and Y are not both N. In another group of embodiments, $R^3$ is H, and each $R^2$ is independently selected from $C_{1-8}$ alkyl, $C_{1-8}$ haloalkyl, halogen and —CN.

In another group of embodiments, the compounds provided herein have the formula (Ia):

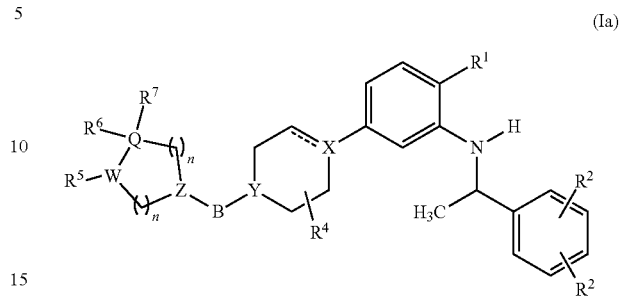

(Ia)

wherein each of $R^1$, $R^2$, $R^4$, $R^5$, $R^6$, $R^7$, X, Y, Z, W, Q, B and the subscripts n, are as described for formula I. In selected embodiments, X is C or CH.

In another group of embodiments, the compounds provided herein have the formula (Ib):

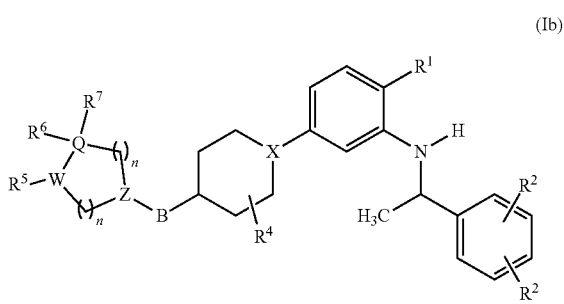

(Ib)

wherein each $R^2$ is selected from $C_{1-8}$ alkyl, $C_{1-8}$ haloalkyl, halogen and —CN, and each of $R^1$, $R^4$, $R^5$, $R^6$, $R^7$, X, Z, W, Q, B and the subscripts n, are as described for formula I.

In another group of embodiments, the compounds provided herein have the formula (IC):

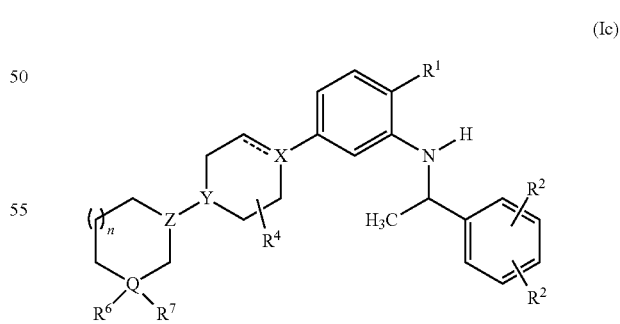

(Ic)

wherein each $R^2$ is selected from $C_{1-8}$ alkyl, $C_{1-8}$ haloalkyl, halogen and —CN; the subscript n is 0 or 1; and each of $R^1$, $R^4$, $R^6$, $R^7$, X, Y, Z, and Q, are as described for formula I. In selected embodiments, n is 1, and $R^4$ is hydrogen or methyl.

In another group of embodiments, the compounds provided herein have the formula (Id):

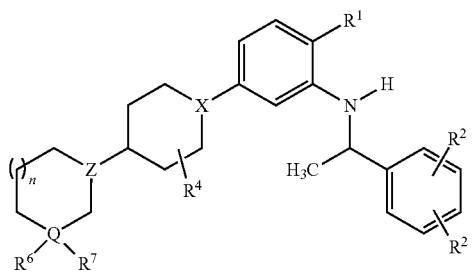

(Id)

wherein each R² is a member selected from C₁₋₈ alkyl, C₁₋₈ haloalkyl, halogen and —CN; the subscript n is 0 or 1, and each of R¹, R⁴, R⁶, R⁷, X, Z, and Q, are as described for formula I. In selected embodiments, n is 1, and R⁴ is hydrogen or methyl.

In another group of embodiments, the compounds provided herein have the formula (Ie):

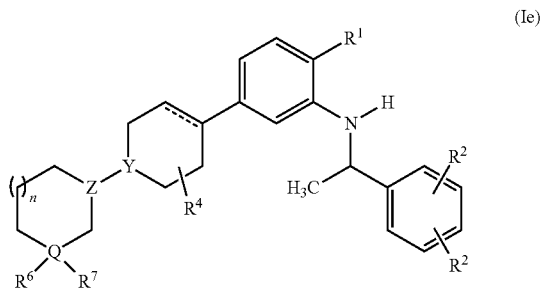

(Ie)

wherein each R² is selected from C₁₋₈ alkyl, C₁₋₈ haloalkyl, halogen and —CN; the subscript n is 0 or 1; and each of R¹, R⁴, R⁶, R⁷, Y, Z, and Q, are as described for formula I. In selected embodiments, n is 1, and R⁴ is hydrogen or methyl.

In another group of embodiments, the compounds provided herein have the formula (If):

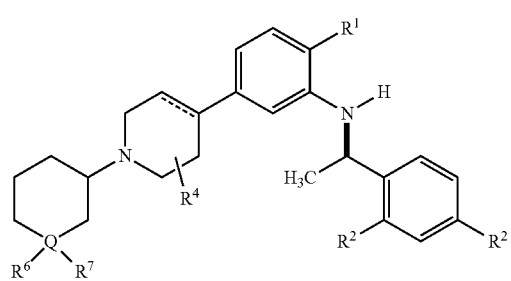

(If)

wherein each R² is selected from C₁₋₈ alkyl, C₁₋₈ haloalkyl, halogen and —CN; and each of R¹, R⁴, R⁶, R⁷, and Q, are as described for formula I. In selected embodiments, R⁴ is hydrogen or methyl.

In still other embodiments, compounds are provided having formulae (I), (Ia), and (Ib), including specific embodiments provided above, wherein B is C(O). Still further, compounds are provided wherein the ring having Z as a ring vertex is selected from pyrrolidine and piperidine. In selected embodiments, compounds are provided wherein the ring having Z as a ring vertex is selected from pyrrolidin-2-yl and piperidin-2-yl, and at least one of R⁵, R⁶ and R⁷ is other than hydrogen In yet other embodiments, compounds are provided having formulae (I), (Ia), and (Ib), including specific embodiments provided above, wherein B is a bond. In related embodiments, B is a bond and the ring having Z as a ring vertex is selected from pyrrolidine, piperidine and cyclohexane. In specific embodiments, B is a bond and the ring having Z as a ring vertex is selected from pyrrolidin-1-yl, pyrrolidin-2-yl, piperidin-1-yl, piperidin-2-yl, piperidin-3-yl and cyclohexane. In still other embodiments, B is a bond and the ring having Z as a ring vertex is selected from the group consisting of pyrrolidin-1-yl, pyrrolidin-2-yl, piperidin-1-yl, piperidin-2-yl, piperidin-3-yl and cyclohexane; and at least one of R⁵, R⁶ and R⁷ is other than hydrogen.

In one group of embodiments, Z is CH or N.

In some embodiments, the CCR4 antagonist has the formula

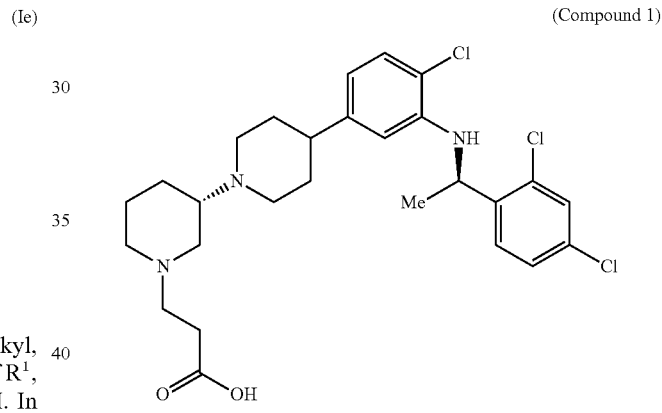

(Compound 1)

or a pharmaceutically acceptable salt thereof.

In some embodiments, the CCR4 antagonist has the formula

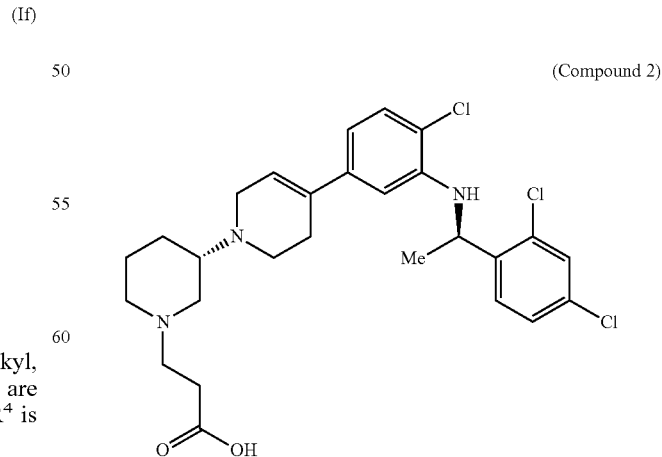

(Compound 2)

or a pharmaceutically acceptable salt thereof.

In some embodiments, the CCR4 antagonist has the formula (Compound 3)

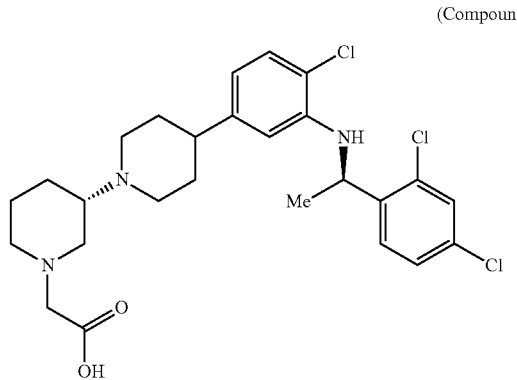

or a pharmaceutically acceptable salt thereof.

In some embodiments, the CCR4 antagonist has the formula (Compound 4)

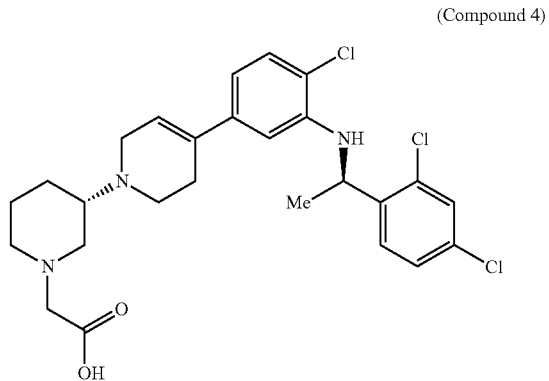 [SMILES: C[C@@H](Nc1cc(C2=CCN([C@H]3CCCN(CC(=O)O)C3)CC2)ccc1Cl)c1ccc(Cl)cc1Cl]

or a pharmaceutically acceptable salt thereof.

In some embodiments, the CCR4 antagonist is selected from the compounds or pharmaceutical compositions disclosed in WO 2013/082490 filed by ChemoCentryx. The contents of which is incorporated herein for all purposes.

B. Immune Checkpoint Inhibitors

Immune checkpoints are signaling proteins that stimulate or inhibit an immune response. Compositions that target immune checkpoints modulate these proteins to alter an individuals natural immune response. This targeted approach is useful because particular cancer cells can circumvent these checkpoints to evade an otherwise natural immune response. Two particular immune checkpoints are programmed cell death protein 1 (PD-1) and cytotoxic T-lymphocyte-associated protein 4 (CTLA-4).

i. PD-1 Inhibitors

Programmed cell death protein-1 (PD-1) is an immune checkpoint protein most commonly found on T cells. Normally, PD-1 binds to its natural ligands PD-L1 and PD-L2, expressed on the surface of different cells. When associated its natural ligand, the T cells is considered to be in the "off" position. Notably, number of cancer cells express unusually high levels of PD-L1, meaning that T cell activity and associated anticancer immune response is aberrantly suppressed. Critically, the use of PD-1 inhibitors that blocks the interaction with it's natural ligands stimulates an immune response to help fight the cancer.

PD-1 inhibitors of the present disclosure include small molecules and antibodies.

In some embodiments, the PD-1 inhibitor is a small molecule PD-1/PD-L1 inhibitor.

In some embodiments, the small molecule PD-1/PD-L1 inhibitor has the formula:

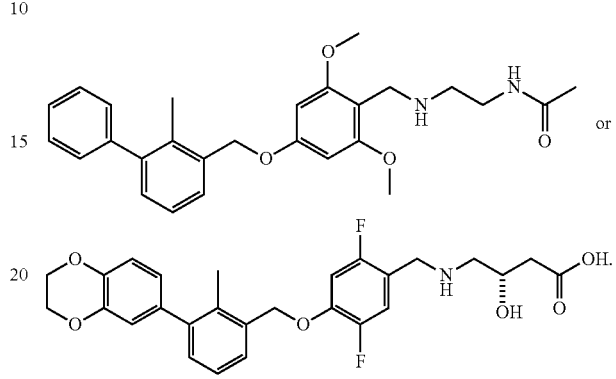

In some embodiments, the small molecule PD-1/PD-L1 inhibitor is a compound having the Formula (II)

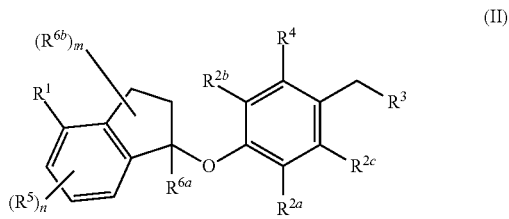

or a pharmaceutically acceptable salt thereof; wherein:

$R^1$ is selected from the group consisting of halogen, $C_{5-8}$ cycloalkyl, $C_{6-10}$ aryl and thienyl,
  wherein the $C_{6-10}$ aryl and thienyl are optionally substituted with 1 to 5 $R^x$ substituents;

each $R^x$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$, and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^x$ substituents are on adjacent atoms, they are combined to form a fused five, six or seven-membered carbocyclic or heterocyclic ring optionally substituted with from 1 to 3 substituents independently selected from halo, oxo, $C_{1-8}$haloalkyl and $C_{1-8}$ alkyl;

each $R^{2a}$, $R^{2b}$ and $R^{2c}$ is independently selected from the group consisting of H, halogen, —CN, —$R^d$, —$CO_2R^e$, —$CONR^eR^f$, —C(O)$R^e$, —OC(O)$NR^eR^f$, —$NR^fC(O)R^e$, —$NR^fC(O)_2R^d$, —$NR^e$—C(O)$NR^eR^f$, —$NR^eR^f$, —O—$X^2$—$OR^e$, —O—$X^2$—$NR^eR^f$, —O—$X^2$—$CO_2R^e$, —O—$X^2$—$CONR^eR^f$, —$X^2$—$OR^e$, —$X^2$—$NR^eR^f$, —$X^2$—$CO_2R^e$, —$X^2$—$CONR^eR^f$, —$SF_5$, —$S(O)_2NR^eR^f$, $C_{6-10}$ aryl and $C_{5-10}$ heteroaryl, wherein each $X^2$ is a $C_{1-4}$ alkylene; each $R^e$ and $R^f$ is independently selected from hydrogen, $C_{1-8}$ alkyl, and $C_{1-8}$haloalkyl, or when attached to the same nitrogen atom can be combined with the nitrogen atom to form a five or six-membered ring having from 0 to 2 additional heteroatoms as ring members selected from N, O and S, and optionally substituted with oxo; each $R^d$ is independently selected from the group consisting of $C_{1-8}$ alkyl, $C_{2-8}$ alkenyl, and $C_{1-8}$haloalkyl;

$R^3$ is selected from the group consisting of —$NR^gR^h$ and $C_{4-12}$ heterocyclyl, wherein the $C_{4-12}$ heterocyclyl is optionally substituted with 1 to 6 $R^y$;

each $R^y$ is independently selected from the group consisting of halogen, —CN, —$CO_2R^j$, —$CONR^jR^k$, —$CONHC_{1-6}$ alkyl-OH, —C(O)$R^j$, —OC(O)$NR^jR^k$, —$NR^jC(O)R^k$, —$NR^jC(O)_2R^k$, CONOH, $PO_3H_2$, —$NR^j$—$C_{1-6}$ alkyl-C(O)$R^k$, —$NR^jC(O)NR^jR^k$, —$NR^jR^k$, —$OR^j$, —$S(O)_2NR^jR^k$, —O—$C_{1-6}$ alkyl-$NR^jR^k$, —O—$C_{1-6}$ alkyl-$CO_2R^j$, —O—$C_{1-6}$ alkyl-$CONR^jR^k$, —$C_{1-6}$ alkyl-$OR_j$, —$C_{1-6}$ alkyl-$NR^jR^k$, —$C_{1-6}$alkyl-$CO_2R^j$, —$C_{1-6}$ alkyl-$CONR^jR^k$, and $SF_5$, wherein the $C_{1-6}$ alkyl portion of $R^y$ is optionally further substituted with OH, $SO_2NH_2$, $CONH_2$, CONOH, $PO_3H_2$, COO—$C^{1-8}$alkyl or $CO_2H$, wherein each $R^j$ and $R^k$ is independently selected from hydrogen, $C_{1-8}$ alkyl optionally substituted with 1 to 2 substituents selected from OH, $SO_2NH_2$, $CONH_2$, CONOH, $PO_3H_2$, COO—$C_{1-8}$alkyl or $CO_2H$, and $C_{1-8}$ haloalkyl optionally substituted with 1 to 2 substituents selected from OH, $SO_2NH_2$, $CONH_2$, CONOH, $PO_3H_2$, COO—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^t$ is independently selected from the group consisting of —OH, $C_{1-8}$ alkyl, $C_{2-8}$ alkenyl, and $C_{1-8}$haloalkyl each of which may be optionally substituted with OH, $SO_2NH_2$, $CONH_2$, CONOH, $PO_3H_2$, COO—$C_{1-8}$alkyl or $CO_2H$;

$R^g$ is selected from the group consisting of H, $C_{1-8}$haloalkyl and $C_{1-8}$ alkyl;

$R^h$ is selected from —$C_{1-8}$ alkyl, $C_{1-8}$haloalkyl, $C_{1-8}$ alkyl-COOH, $C_{1-8}$ alkyl-OH, $C_{1-8}$ alkyl-$CONH_2$, $C_{1-8}$ alkyl-$SO_2NH_2$, $C_{1-8}$ alkyl-$PO_3H_2$, $C_{1-8}$ alkyl-CONOH, $C_{1-8}$ alkyl-$NR^{h1}R^{h2}$, —C(O)—$C_{1-8}$ alkyl, —C(O)—$C_{1-8}$ alkyl-OH, —C(O)—$C_{1-8}$ alkyl-COOH, $C_{3-10}$ cycloalkyl, —$C_{3-10}$ cycloalkyl-COOH, —$C_{3-10}$ cycloalkyl-OH, $C_{4-8}$ heterocyclyl, —$C_{4-8}$ heterocyclyl-COOH, —$C_{4-8}$ heterocyclyl-OH, —$C_{1-8}$ alkyl-$C_{4-8}$ heterocyclyl, —$C_{1-8}$ alkyl-$C_{3-10}$ cycloalkyl, $C_{5-10}$ heteroaryl, —$C_{1-8}$ alkyl-$C_{5-10}$ heteroaryl, $C_{10}$ carbocyclyl, —$C_{1-8}$ alkyl-$C_{6-10}$ aryl, —$C_{1-8}$ alkyl-(C=O)—$C_{6-10}$ aryl, —$C_{1-8}$ alkyl-NH(C=O)—$C_{1-8}$ alkenyl, —$C_{1-8}$ alkyl-NH(C=O)—$C_{1-8}$ alkyl, —$C_{1-8}$ alkyl-NH(C=O)—$C_{1-8}$ alkynyl, —$C_{1-8}$ alkyl-(C=O)—NH—$C_{1-8}$ alkyl-COOH, and —$C_{1-8}$ alkyl-(C=O)—NH—$C_{1-8}$ alkyl-OH optionally substituted with $CO_2H$; or $R^h$ combined with the N to which it is attached is a mono-, di- or tri-peptide comprising 1-3 natural amino acids and 0-2 non-natural amino acids, wherein the non-natural aminoacids have an alpha carbon substituent selected from the group consisting of $C_{2-4}$ hydroxyalkyl, $C_{1-3}$ alkyl-guanidinyl, and $C_{1-4}$ alkyl-heteroaryl, the alpha carbon of each natural or non-natural amino acids are optionally further substituted with a methyl group, and the terminal moiety of the mono-, di-, or tri-peptide is selected from the group consisting of C(O)OH, C(O)O—$C_{1-6}$ alkyl, and $PO_3H_2$, wherein $R^{h1}$ and $R^{h2}$ are each independently selected from the group consisting of H, $C_{1-6}$ alkyl, and $C_{1-4}$ hydroxyalkyl;

the $C_{1-8}$ alkyl portions of $R^h$ are optionally further substituted with from 1 to 3 substituents independently selected from OH, COOH, $SO_2NH_2$, $CONH_2$, CONOH, COO—$C_{1-8}$ alkyl, $PO_3H_2$ and $C_{5-6}$ heteroaryl optionally substituted with 1 to 2 $C_{1-3}$ alkyl substituents, the $C_{10}$ carbocyclyl, $C_{5-10}$ heteroaryl and the $C_{6-10}$ aryl portions of $R^h$ are optionally substituted with 1 to 3 substituents independently selected from OH, $B(OH)_2$, COOH, $SO_2NH_2$, $CONH_2$, CONOH, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-CONOH, $C_{1-4}$ alkyl-$PO_3H_2$, $C_{1-4}$alkyl-COOH, and phenyl and the $C_{4-8}$ heterocyclyl and $C_{3-10}$ cycloalkyl portions of $R^h$ are optionally substituted with 1 to 4 $R^w$ substituents;

each $R^w$ substituent is independently selected from $C_{1-4}$ alkyl, $C_{1-4}$ alkyl-OH, $C_{1-4}$ alkyl-COOH, $C_{1-4}$ alkyl-$SO_2NH_2$, $C_{1-4}$ alkyl $CONH_2$, $C_{1-4}$ alkyl-CONOH, $C_{1-4}$ alkyl-$PO_3H$, OH, COO—$C_{1-8}$alkyl, COOH, $SO_2NH_2$, $CONH_2$, CONOH, $PO_3H_2$ and oxo;

$R^4$ is selected from the group consisting of O—$C_{1-8}$ alkyl, O—$C_{1-8}$haloalkyl, O—$C_{1-8}$ alkyl-$R^z$, $C_{6-10}$ aryl, $C_{5-10}$ heteroaryl, —O—$C_{1-4}$ alkyl-$C_{6-10}$aryl and —O—$C_{1-4}$ alkyl-$C_{5-10}$ heteroaryl, wherein the $C_{6-10}$ aryl and the $C_{5-10}$ heteroaryl are optionally substituted with 1 to 5 $R^z$;

each $R^z$ is independently selected from the group consisting of halogen, —CN, —$R^m$, —$CO_2R^n$, —$CONR''R^p$, —C(O)$R^n$, —OC(O)$NR''R^p$, —$NR''C(O)R^p$, —$NR''C(O)_2R^m$, —$NR''$—C(O)$NR''R^p$, —$NR''R^p$, —$OR''$, —O—$X^3$—$OR''$, —O—$X^3$—$NR''R^p$, —O—$X^3$—$CO_2R''$, —O—$X^3$—$CONR''R^p$, —$X^3$—$OR''$, —$X^3$—$NR''R^p$, —$X^3$—$CO_2R''$, —$X^3$—$CONR''R^p$, —$SF_5$, —$S(O)_2R''R^p$, —$S(O)_2NR''R^p$, and three to seven-membered carbocyclic or four to seven-membered heterocyclic ring wherein the three to seven-membered carbocyclic or four to seven-membered heterocyclic ring is optionally substituted with 1 to 5 $R^t$, wherein each $R^t$ is independently selected from the group consisting of $C_{1-8}$ alkyl, $C_{1-8}$haloalkyl, —$CO_2R''$, —$CONR''R^p$, —C(O)$R''$, —OC(O)$NR''R^p$, —$NR''C(O)R^p$, —$NR''C(O)_2R'''$, —$NR''$—C(O)$NR''R^p$, —$OR''$, —O—$X^3$—$OR''$, —O—$X^3$—$NR''R^p$, —O—$X^3$—$CO_2R''$, —O—$X^3$—$CONR''R^p$, —$X^3$—$OR''$, —$X^3$—$NR''R^p$, —$X^3$—$CO_2R''$, —$X^3$—$CONR''R^p$, —$SF_5$, and —$S(O)_2NR''R^p$;

wherein each $X^3$ is a $C_{1-4}$ alkylene; each $R^n$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each WI is independently selected from the group consisting of $C_{1-8}$ alkyl, $C_{2-8}$ alkenyl, and $C_{1-8}$ haloalkyl; and optionally when two W substituents are on adjacent atoms, they are combined to form a fused five or six-membered carbocyclic or heterocyclic ring optionally substituted with oxo;

n is 0, 1, 2 or 3;

each $R^5$ is independently selected from the group consisting of halogen, —CN, —$R^q$, —$CO_2R^r$, —$CONR'R^s$, —C(O)$R^r$, —OC(O)$NR'R^s$, —$NR'C(O)R^s$, —$NR'C(O)_2R^q$, —$NR^r$—C(O)$NR'R^s$, —$NR'R^s$, —$OR^r$, —O—$X^4$—$OR^r$, —O—$X^4$—$NR'R^s$, —O—$X^4$—$CO_2R^r$, —O—$X^4$—$CONR'R^s$, —$X^4$—$OR^r$, —$X^4$—$NR'R^s$, —$X^4$—$CO_2R^r$, —$SF_5$, —$S(O)_2NR'R^s$, wherein each $X^4$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each Rq is independently selected from the group consisting of $C_{1-8}$ alkyl, and $C_{1-8}$ haloalkyl;

$R^{6a}$ is selected from the group consisting of H, $C_{1-4}$ alkyl and $C_{1-4}$ haloalkyl;

each $R^{6b}$ is independently selected from the group consisting of F, $C_{1-4}$ alkyl, O—$R^u$, $C_{1-4}$ haloalkyl, $NR^uR^v$, wherein each $R^u$ and $R^v$ is independently selected from hydrogen, $C_{1-8}$ alkyl, and $C_{1-8}$haloalkyl, or when attached to the same nitrogen atom can be combined with the nitrogen atom to form a five or six-membered ring having from 0 to 2 additional heteroatoms as ring members selected from N, O or S, and optionally substituted with oxo; and m is 0, 1, 2, 3 or 4.

In some embodiments, the compound, or a pharmaceutically acceptable salt thereof has the formula (IIa)

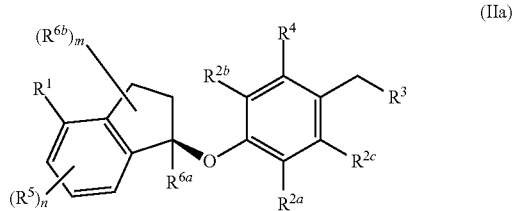

(IIa)

In some embodiments, the compound, or a pharmaceutically acceptable salt thereof having the formula (IIb)

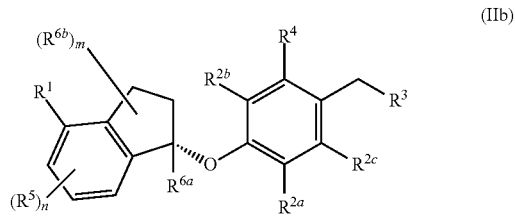

(IIb)

In some embodiments, $R^1$ is selected from the group consisting of phenyl and thienyl, wherein the phenyl and thienyl are optionally substituted with 1 to 5 $R^x$ substituents. In some embodiments, $R^1$ is phenyl optionally substituted with 1 or 2 $R^x$ wherein each $R^x$ is independently selected from halogen, $C_{1-8}$ alkyl, O—$C_{1-8}$ alkyl, O—$C_{1-8}$ haloalkyl, —$NR^aR^b$, and CN, and optionally when two $R^x$ substituents are on adjacent atoms, they are combined to form a fused six-membered heterocyclic ring optionally substituted with from 1 to 3 substituents independently selected from oxo, $C_{1-8}$ haloalkyl and $C_{1-8}$ alkyl. In some embodiments, $R^1$ is phenyl optionally substituted with F. In some embodiments, $R^1$ is selected from the group consisting of:

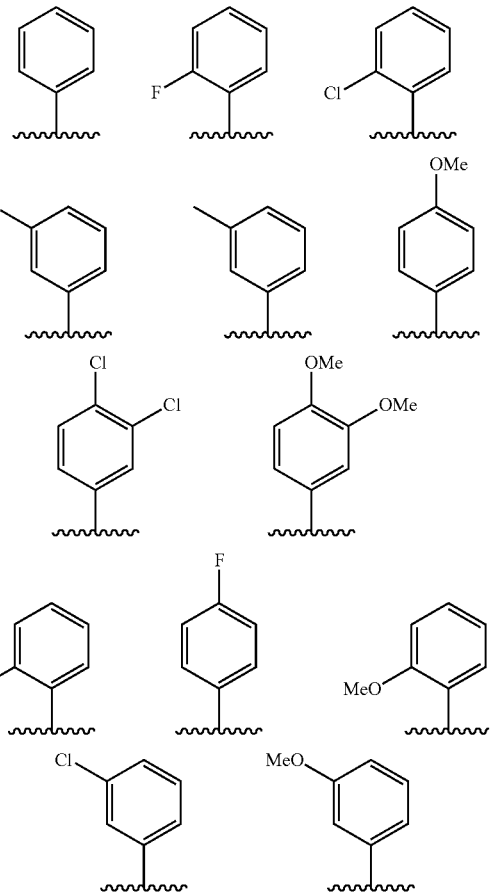

-continued

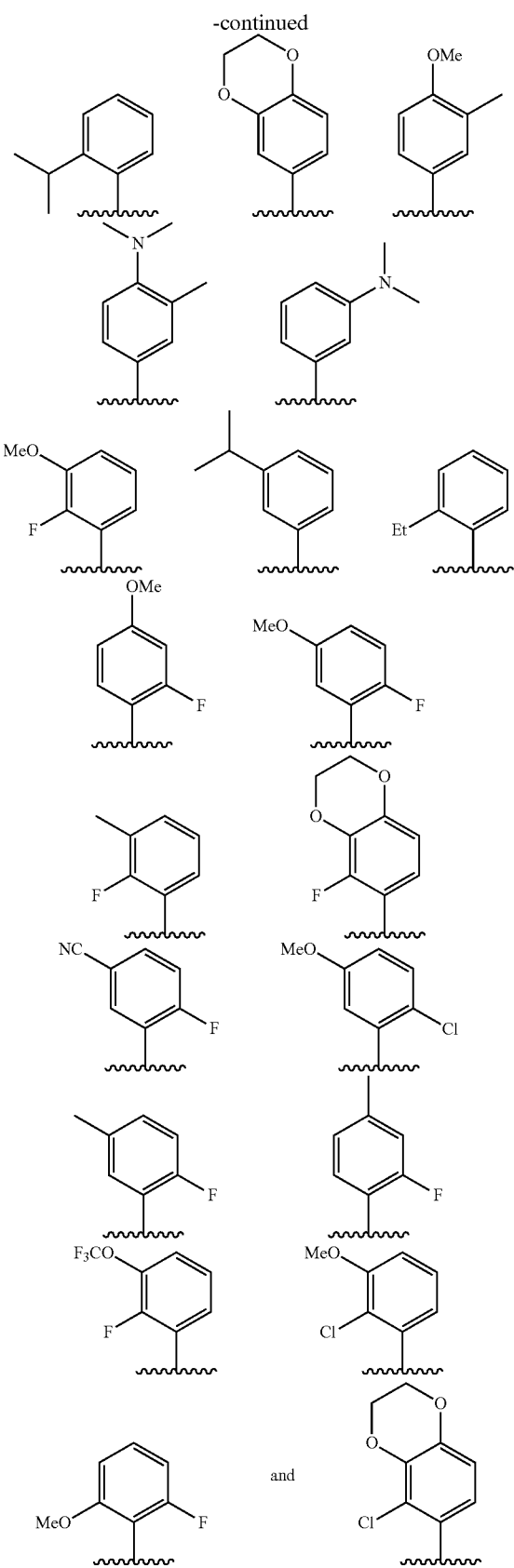

In some embodiments, each $R^{2a}$, $R^{2b}$ and $R^{2c}$ is independently selected from the group consisting of H, halogen, —CN, —$R^d$, —$NR^eR^f$, —$OR_e$, —$X^2$—$NR^eR^f$, —$X^2$—$NR^eR^f$, wherein $X^2$ is $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl. In some embodiments, $R^{2b}$ and $R^{2c}$ are both H and $R^{2a}$ is selected from the group consisting of halogen, $C_{1-4}$ alkyl, $C_{2-4}$ alkenyl, $C_{1-3}$ haloalkyl, —CN, —OMe and OEt. In some embodiments, $R^{2b}$ and $R^{2c}$ are both H and $R^{2a}$ is halogen. In some embodiments, $R^{2b}$ and $R^{2c}$ are both H and $R^{2a}$ is Cl.

In some embodiments, n is 0, 1 or 2 and each $R^5$ is independently selected from the group consisting of halogen, —CN, —$R^q$, —$NR^rR^s$, and —$OR^r$, wherein each $R^r$ and $R^s$ is independently selected from hydrogen, $C_{1-8}$ alkyl and $C_{1-8}$ haloalkyl and each $R^q$ is independently selected from the group consisting of $C_{1-8}$ alkyl and $C_{1-8}$ haloalkyl. In some embodiments, n is 0.

In some embodiments, $R^{6a}$ is H. In some embodiments, m is 0. In some embodiments, m is 1 and $R^{6b}$ is selected from the group consisting of F, $C_{1-4}$ alkyl, O—$R^u$, $C_{1-4}$ haloalkyl and $NR^uR^v$, wherein each $R^u$ and $R^v$ is independently selected from hydrogen, $C_{1-8}$ alkyl, and $C_{1-8}$ haloalkyl. In some embodiments, m is 1 and $R^{6b}$ is F.

In some embodiments,

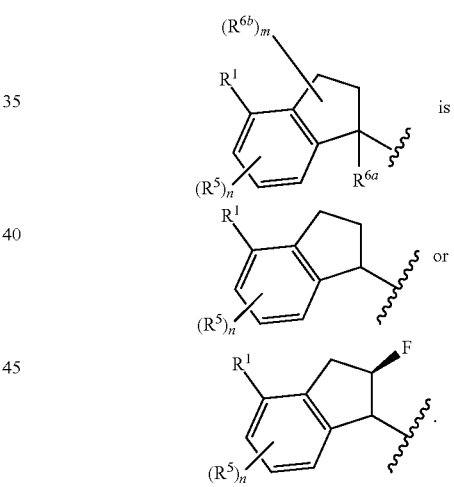

In some embodiments,

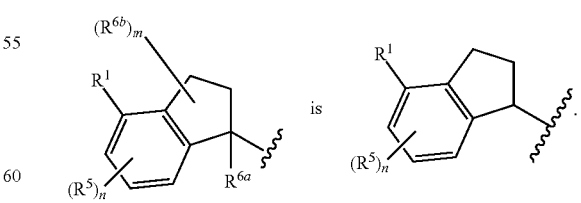

In some embodiments, $R^4$ is selected from the group consisting of O—$C_{1-4}$ alkyl, O—$C_{1-6}$ alkyl-$R^z$, $C_{6-10}$ aryl, $C_{5-10}$ heteroaryl, —O—$C^{1-4}$ alkyl-$C_{6-10}$aryl and —O—$C_{1-4}$alkyl-$C_{5-10}$ heteroaryl, wherein the $C_{6-10}$ aryl and the $C_{5-10}$ heteroaryl are optionally substituted with 1 to 2 $R^z$, wherein each $R^z$ is independently selected from the group consisting of halogen, —CN, —$R^m$, —$CO_2R''$, —$CONR''R^p$, —C(O)$R''$, —OC(O)NR''$R^p$, —NR''C(O)$R^p$, —NR''C(O)$_2R^p$, —NR''—C(O)NR''$R^p$, —NR''$R^p$, —$OR_n$, —S(O)$_2$NR''$R^p$, three to seven-membered carbocyclic ring and four to seven-membered heterocyclic ring wherein the three to seven-membered carbocyclic or four to seven-membered heterocyclic ring is optionally substituted with 1 to 2 $R^t$, wherein each $R^t$ is independently selected from the group consisting of $C_{1-8}$ alkyl, $C_{1-8}$ haloalkyl, —$CO_2R''$, —$CONR''R^p$, —C(O)$R''$, —OC(O)NR''$R^p$, —NR''C(O)$R^p$, —NR''C(O)$_2R^m$, —NR''—C(O)NR''$R^p$, —NR''$R^p$, —$OR''$, and —S(O)$_2$NR''$R^p$. In some embodiments, $R^4$ is selected from the group consisting of O—$C_{1-4}$ alkyl, O—$C_{1-6}$ alkyl-CN, phenyl, pyridinyl, —O—$C_{1-2}$ alkyl-pyridinyl, —O—$C_{1-2}$ alkyl-pyrimidinyl, $C_{1-2}$ alkyl-pyridazinyl, and —O—$C_{1-2}$ alkyl-phenyl, wherein the pyridinyl, phenyl, pyrimidinyl and pyridazinyl is optionally substituted with 1 to 2 $R^z$, wherein each $R^z$ is independently selected from the group consisting of halogen, —CN, —$CO_2R''$, —NR''$R^p$, —$OR''$, and piperidinyl optionally substituted with OH.

In some embodiments, $R^4$ is selected from the group consisting of:

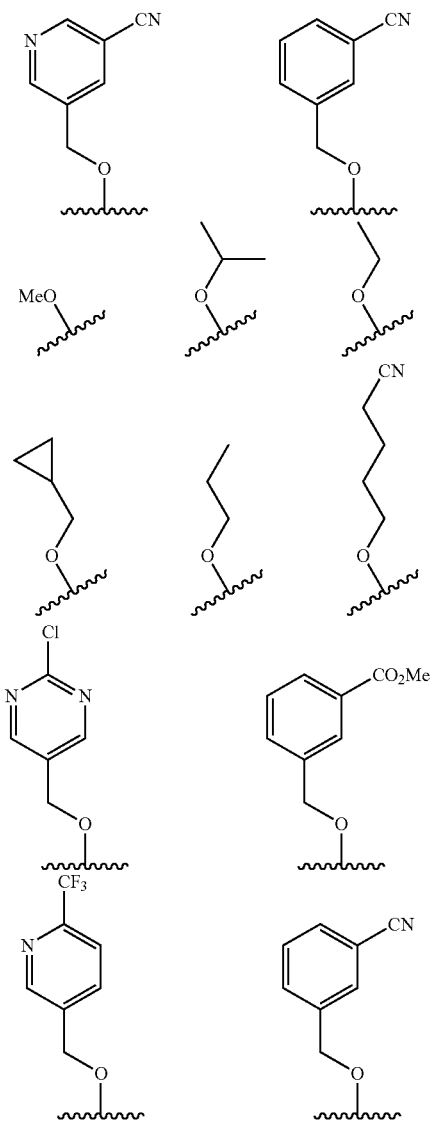

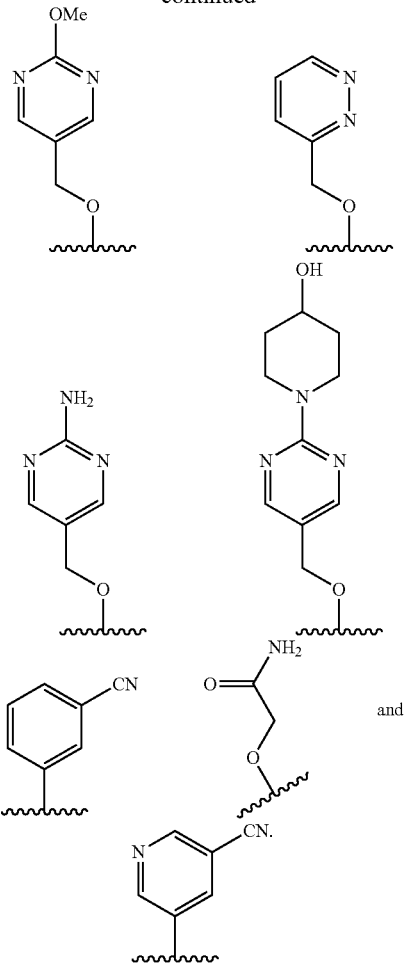

In some embodiments, $R^4$ is

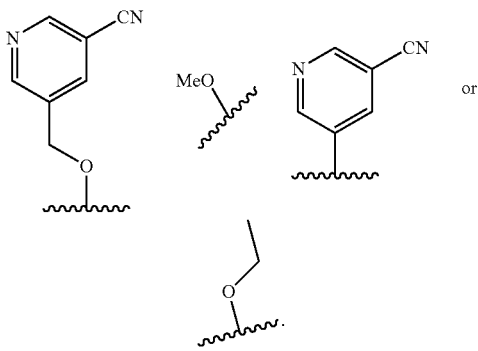

In some embodiments, $R^3$ is selected from the group consisting of $NR^gR^h$ and $C_{4-6}$ heterocyclyl wherein the $C_{4-6}$ heterocyclyl is optionally substituted with 1 to 3 $R^y$, wherein $R^g$ is selected from the group consisting of H, $C_{1-8}$ haloalkyl and $C_{1-8}$ alkyl, and wherein $R^h$ is —$C_{1-8}$ alkyl substituted with from 1 to 3 substituents independently selected from OH, COOH, SO$_2$NH$_2$, CONH$_2$, CONOH, COO—$C_{1-8}$ alkyl, $C_{5-6}$ heteroaryl, $C_{5-6}$ heterocyclyl and PO$_3$H$_2$, wherein the $C_{5-6}$ heteroaryl and the $C_{5-6}$ heterocyclyl are optionally substituted with 1 to 3 substituents independently selected from OH, B(OH)$_2$, COOH, SO$_2$NH$_2$, CONH$_2$, CONOH, PO$_3$H$_2$, COO—C$_{1-8}$ alkyl, C$_{1-4}$ alkyl, C$_{1-4}$alkyl-OH, C$_{1-4}$alkyl-SO$_2$NH$_2$, C$_{1-4}$alkyl CONH$_2$, C$_{1-4}$alkyl-CONOH, C$_{1-4}$ alkyl-PO$_3$H$_2$, and C$_{1-4}$ alkyl-COOH and wherein the C$_{5-6}$ heterocyclyl is additionally optionally substituted with oxo. In some embodiments, R$^3$ is selected from the group consisting of azetidinyl, pyrrolidinyl and piperidinyl, wherein the azetidinyl, pyrrolidinyl or piperidinyl is linked through the nitrogen atom and wherein the azetidinyl, pyrrolidinyl or piperidinyl is optionally substituted with 1 to 3 BY, wherein each R$^y$ is independently selected from the group consisting of —CO$_2$H, CONOH, PO$_3$H$_2$, OH, SO$_2$NH$_2$, CONH$_2$, and COO—C$_{1-8}$alkyl. In some embodiments, R$^3$ is NHR$^h$, wherein R$^h$ is —C$_{1-8}$ alkyl substituted with from 1 to 2 substituents independently selected from OH, COOH, CONH$_2$, PO$_3$H$_2$, tetrazolyl, tetrazolonyl, and pyrazolyl. In some embodiments, R$^3$ is selected from the group consisting of:

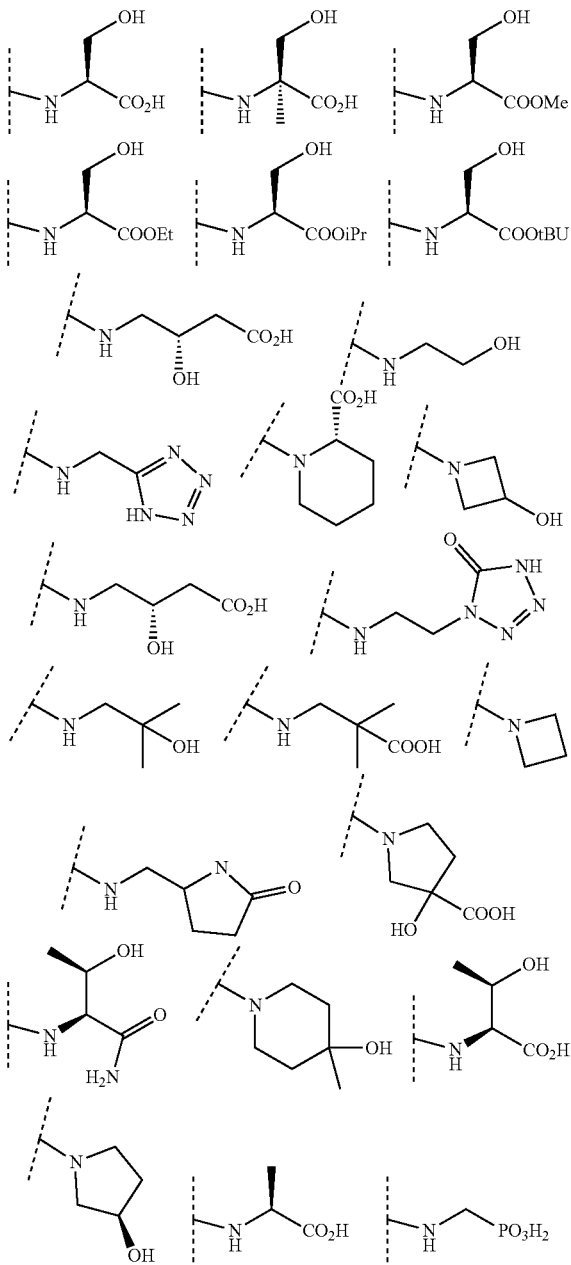

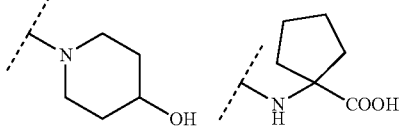

-continued

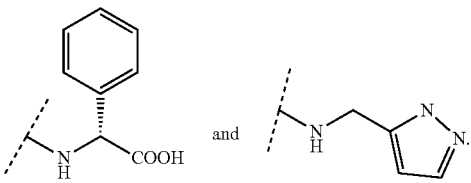

and

In some embodiments, R$^3$ is —NR$^g$R$^h$. In some embodiments, R$^h$ combined with the N to which it is attached is a mono-, di- or tri-peptide comprising 1-3 natural amino acids and 0-2 non-natural amino acids, wherein
  the non-natural aminoacids have an alpha carbon substituent selected from the group consisting of C$_{2-4}$ hydroxyalkyl, C$_{1-3}$ alkyl-guanidinyl, and C$_{1-4}$ alkyl-heteroaryl,
  the alpha carbon of each natural or non-natural amino acids are optionally further substituted with a methyl group, and
  the terminal moiety of the mono-, di-, or tri-peptide is selected from the group consisting of C(O)OH, C(O)O—C$_{1-6}$ alkyl, and PO$_3$H$_2$.

In some embodiments, each natural amino acid of R$^h$ is independently selected from the group consisting of serine, alanine, glycine, lysine, argining, threonine, phenylalanine, tyrosine, asparatate, asparagine, histidine, and leucine.

In some embodiments, le is phenyl optionally substituted with 1 to 3 R$^x$, R$^{6a}$ is H, R$^4$ is selected from the group consisting of O—C$_{1-4}$ alkyl, O—C$_{1-6}$ alkyl-CN, phenyl, pyridinyl, —O—C$_{1-2}$ alkyl-pyridinyl, —O—C$_{1-2}$ alkyl-pyrimidinyl, —O—C$_{1-2}$ alkyl-pyridazinyl, and —O—C$_{1-2}$ alkyl-phenyl, wherein the pyridinyl, phenyl, pyrimidinyl and pyridazinyl is optionally substituted with 1 to 2 R$^z$, wherein each R$^z$ is independently selected from the group consisting of halogen, —CN, —CO$_2$R$^n$, —NR$^n$R$^p$, —OR$_n$, and piperidinyl optionally substituted with OH, and R$^3$ is selected from the group consisting of NR$^g$R$^h$ and C$_{4-6}$ heterocyclyl wherein the C$_{4-6}$ heterocyclyl is optionally substituted with 1 to 3 R$^y$, wherein R$^g$ is selected from the group consisting of H, C$_{1-8}$ haloalkyl and C$_{1-8}$ alkyl, and wherein R$^h$ is —C$_{1-8}$ alkyl substituted with from 1 to 3 substituents independently selected from OH, COOH, SO$_2$NH$_2$, CONH$_2$, CONOH, COO—C$_{1-8}$ alkyl, C$_{5-6}$ heteroaryl, C$_{5-6}$ heterocyclyl and PO$_3$H$_2$, wherein the C$_{5-6}$ heteroaryl and the C$_{5-6}$ heterocyclyl are optionally substituted with 1 to 3 substituents independently selected from OH, B(OH)$_2$, COOH, SO$_2$NH$_2$, CONH$_2$, CONOH, PO$_3$H$_2$, COO—C$_{1-8}$alkyl, C$_{1-4}$alkyl, C$_{1-4}$alkyl-OH, C$_{1-4}$alkyl-SO$_2$NH$_2$, C$_{1-4}$alkyl CONH$_2$, C$_{1-4}$ alkyl-CONOH, C$_{1-4}$ alkyl-PO$_3$H$_2$, and C$_{1-4}$ alkyl-COOH and wherein the C$_{5-6}$ heterocyclyl is additionally optionally substituted with oxo.

In some embodiments, le is phenyl optionally substituted with 1 or 2 R$^x$ wherein each R$^x$ is independently selected from halogen, C$_{1-8}$ alkyl, O—C$_{1-8}$alkyl, O—C$_{1-8}$haloalkyl, —NR$^a$R$^b$, and CN, wherein R$^{2b}$ and R$^{2c}$ are both H, R$^{2a}$ is selected from the group consisting of halogen, $C_{1-4}$ alkyl, $C_{1-3}$ haloalkyl, —CN, —OMe and OEt, $R^{6a}$ is H, m is 0, n is 0, $R^4$ is

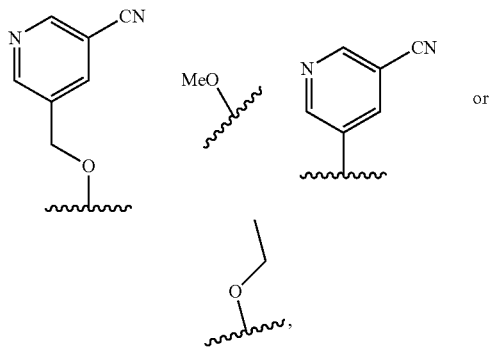

and $R^3$ is selected from the group consisting of $NHR^h$, azetidinyl, pyrrolidinyl and piperidinyl, wherein the azetidinyl, pyrrolidinyl or piperidinyl is linked through the nitrogen atom and wherein the azetidinyl, pyrrolidinyl or piperidinyl is optionally substituted with 1 to 3 $R^y$, wherein each $R^y$ is independently selected from the group consisting of $CO_2H$, $CONOH$, $PO_3H_2$, OH, $SO_2NH_2$, $CONH_2$, and COO—$C_{1-8}$alkyl, and wherein $R^h$ is $C_{1-8}$ alkyl substituted with from 1 to 2 substituents independently selected from OH, COOH, $CONH_2$, $PO_3H_2$, tetrazolyl, tetrazolonyl, and pyrazolyl. In some embodiment, $R^{2a}$ is halogen.

In some embodiments, the small molecule PD-1/PD-L1 inhibitor is selected from the compounds or pharmaceutical compositions disclosed in WO 2018/005374 filed by ChemoCentryx on Jun. 26, 2017. The contents of which is incorporated herein for all purposes.

In some embodiments, the PD-1 inhibitor is an antibody. In some embodiments, the PD-1 inhibitor antibody is selected from Nivolumab, Pembrolizumab, and Pidilizumab. In some embodiments the PD-1 inhibitor antibody is Nivolumab. In some embodiments the PD-1 inhibitor antibody is Pembrolizumab. In some embodiments the PD-1 inhibitor antibody is Pidilizumab.

The PD-1 inhibitors of the present disclosure can be prepared using known methods in the art. For example, human monoclonal antibodies of this disclosure can be prepared using SCID mice into which human immune cells have been reconstituted such that a human antibody response can be generated upon immunization. Such mice are described in, for example, U.S. Pat. Nos. 5,476,996 and 5,698,767 to Wilson et al. The PD-1 inhibitors of the present disclosure can be formulated to retard the degradation of the compound or antibody or to minimize the immunogenicity of the antibody. A variety of techniques are known in the art to achieve this purposes.

ii. CTLA-4 Inhibitors

Cytotoxic T-lymphocyte-associated protein 4 (CTLA-4) is an immune checkpoint protein most commonly expressed by activated T cells. Like PD-1, CTLA-4 acts as a negative regulator of T-cell immune function. By providing inhibitors of CTLA-4, the negative regulation is reduced and the antitumor activity of T cells is increased.

In some embodiments, the CTLA-4 inhibitor is an antibody. In some embodiments, the CLTA-4 inhibitor antibody has a binding affinity of about $10^8$ $M^{-1}$ or greater. In some embodiments, the CLTA-4 inhibitor antibody has a binding affinity of about $10^9$ $M^{-1}$ or greater. In some embodiments, the CTLA-4 inhibitor antibody inhibits the binding of human CTLA-4 to B7-1 or to B7-2.

In some embodiments, the CTLA-4 inhibitor antibody is selected from Ipilimumab, Tremelimumab, AGEN1884, and AGEN2041. In some embodiments, the CTLA-4 inhibitor antibody is Ipilimumab. In some embodiments, the CTLA-4 inhibitor antibody is Tremelimumab. In some embodiments, the CTLA-4 inhibitor antibody is AGEN1884. In some embodiments, the CTLA-4 inhibitor antibody is AGEN2041.

In some embodiments, the CTLA-4 inhibitor is selected from the compounds or pharmaceutical compositions disclosed in WO/2009/100140 or WO 2017/194265. The contents of each is incorporated herein for all purposes.

The CTLA-4 inhibitors of the present disclosure can be prepared using known methods in the art. For example, human monoclonal antibodies of this disclosure can be prepared using SCID mice into which human immune cells have been reconstituted such that a human antibody response can be generated upon immunization. Such mice are described in, for example, U.S. Pat. Nos. 5,476,996 and 5,698,767 to Wilson et al. The CTLA-4 inhibitors of the present disclosure can also be formulated to retard the degradation of the compound or antibody or to minimize the immunogenicity of the antibody. A variety of techniques are known in the art to achieve this purposes.

IV. Methods of Administration of Combination Therapy

In another aspect, the present disclosure provides a combination therapy for the treatment of cancer. The combination therapy includes a therapeutically effective amount of a CCR4 antagonist and a therapeutically effective amount of one or more immune checkpoint inhibitors. In some embodiments, the one or more immune checkpoint inhibitors is a PD-1 inhibitor. In some embodiments, the one or more immune checkpoint inhibitors is a CTLA-4 inhibitor. In some embodiments, the one or more immune checkpoint inhibitors are a PD-1 inhibitor and a CTLA-4 inhibitor. The combination of therapeutic agents act synergistically to affect the treatment or prevention of cancer.

The term "therapeutically effective amount" means the amount of the subject compound that will elicit the biological or medical response of a cell, tissue, system, or animal, such as a human, that is being sought by the researcher, veterinarian, medical doctor or other treatment provider.

Depending on the disease status and the subject's condition, the compounds, antibodies, and formulations of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration. In addition, the compounds and antibodies may be formulated, alone or together, in suitable dosage unit formulations containing conventional nontoxic pharmaceutically acceptable carriers, adjuvants and vehicles appropriate for each rouse of administration. The present disclosure also contemplates administration of the compounds and antibodies of the present disclosure in a depot formulation.

It will be understood, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

Combination therapy includes co-administration of the CCR4 antagonist and the one or more immune checkpoint inhibitors, sequential administration of the CCR4 antagonist and the one or more checkpoint inhibitors, administration of a composition containing the CCR4 antagonist and the one or more checkpoint inhibitors, or simultaneous administration of separate compositions such that one composition contains the CCR4 antagonist and one or more compositions contain the one or more checkpoint inhibitors. In embodiments where two immune checkpoint inhibitors are administered, it is understood that each immune checkpoint inhibitor can be formulated separately or formulated in a single dosage unit.

Co-administration includes administering the CCR4 antagonist of the present disclosure within 0.5, 1, 2, 4, 6, 8, 10, 12, 16, 20, or 24 hours of the one or more immune checkpoint inhibitors of the present disclosure. Co-administration also includes administering simultaneously, approximately simultaneously (e.g., within about 1, 5, 10, 15, 20, or 30 minutes of each other), or sequentially in any order. Moreover, the CCR4 antagonist and one or more checkpoint inhibitors can each be administered once a day, or two, three, or more times per day so as to provide the preferred dosage level per day.

V. Kits

In some aspects, provided herein are kits containing a CCR4 antagonist and one or more immune check-point inhibitors that are useful for treating a cancer. A kit can contain a pharmaceutical composition containing a CCR4 antagonist compound, e.g., a small molecule inhibitor of CCR4 and one or more pharmaceutical composition containing immune checkpoint inhibitors, e.g., an anti-PD-1 inhibitor and/or an anti-CTLA-4 inhibitor. In some instances, the kit includes written materials e.g., instructions for use of the compound, antibody or pharmaceutical compositions thereof. Without limitation, the kit may include buffers, diluents, filters, needles, syringes, and package inserts with instructions for performing any methods disclosed herein.

VI. Examples

Example 1: C-C Chemokine Receptor 4 (CCR4) Antagonism Enhances the Effectiveness of Checkpoint Inhibition in Mouse Tumor Models (Summary)

Chemokines and their receptors influence many of the hallmark processes in cancer: they act not only on infiltrating leukocytes, but also on fibroblasts, endothelial cells and directly on some types of tumor cells. C-C Chemokine receptor 4 (CCR4) and its ligands have been found to be highly expressed in multiple types of human tumors, and are associated with poor prognosis. CCR4 antagonism has been demonstrated to reduce tumor growth in various mouse tumor models. Here we assess small molecule inhibition of CCR4 as a therapeutic agent to potentiate the effects of checkpoint inhibitors in the CT26 and KCM tumor models.

Methods

The subcutaneous CT26 colon cancer model and the orthotopic KCM pancreatic cancer model were used to assess the effects of a CCR4 inhibitor, Compound 1, in combination with anti-CTLA-4 antibody (BioXcell: anti-mouse CTLA-4 (Clone: 9H10), raised in Syrian Hamster, purified with protein G). CT26 cells were implanted into the flanks of 9 week female Balb/c mice. Mice were randomized into study groups based on the tumor sizes on day 6, and dosing of both Compound 1 and anti-CTLA-4 started on day 7. For the orthotopic pancreatic cancer model, KCM cells were implanted directly into the pancreas, and dosing of Compound 1 and anti-CTLA-4 also began on day 7. Compound 1 was dosed orally twice daily at 30 mg/kg, and anti-CTLA-4 was dosed IP on days 7, 11 and 15 at 100 µg/mouse.

Results

Blockade of CCR4 appreciably enhanced the therapeutic effects of anti-CTLA-4 in both models. Combined anti-CTLA-4/CCR4 inhibitor significantly decreased tumor size and increased the proportion of long-term survivors in the CT26 model. The anti-tumor response was CT26-specific; long term survivors were resistant to re-inoculation with CT26 cells (without further dosing of either drug), but 4T1 breast tumors grew well upon challenge of CT26 survivors. Mice with tumor regression exhibited a high proportion of CD8 T cells that recognized a CT26-specific neoantigen, as illustrated by AH1 peptide-MHC tetramer staining.

Although long term survival has not yet been examined the KCM model, Compound 1 alone significantly reduced tumor burden in 3 independent studies. Anti-CTLA-4 alone provided substantial inhibition of tumor growth in this model, which was further enhanced by Compound 1.

Example 2: Compound 1 is a Highly Potent and Selective CCR4 Inhibitor

The selectivity of Compound 1 was tested by determining the $IC_{50}$ value against a diverse panel of receptors, enzymes, and ion channels. Compound 1 was found to be highly specific for CCR4. See, Table 1.

TABLE 1

| Compound 1 Selectivity | |
| --- | --- |
| Receptor | Buffer $IC_{50}$ (nM) |
| CCR1 | >10,000 |
| CCR2 | >10,000 |
| CCR4 | 2 |
| CCR5 | >10,000 |
| CCR6 | >10,000 |
| CCR7 | >10,000 |
| CCR8 | >10,000 |
| CCR9 | >10,000 |
| CCR10 | >10,000 |
| CCR12 | >10,000 |
| CXCR1 | >10,000 |
| CXCR2 | >10,000 |
| CXCR3 | >10,000 |
| CXCR4 | >10,000 |
| CXCR6 | >10,000 |
| CXCR7 | >10,000 |
| Duffy | >10,000 |

The binding activity of Compound 1 in humans and mice is reported in Table 2.

TABLE 2

Cross Species Activity

| | | Binding IC$_{50}$ (nM) | Chemotaxis A$_2$ (nM) | |
|---|---|---|---|---|
| Species | Cells | Buffer $^{125}$I-CCL17 | Buffer CCL22 | 100% serum CCL22 |
| Human | CEM | 23 | 2 | 20 |
| | Lymphocytes | 37 | 10 | 20 |
| Mouse | mCCR4-Baf3 | | 4 | 60 |
| | mCCR4-293 | 27 | | |

Example 3: Combination Therapy Using a KCM Orthotopic Pancreatic Tumor Model As briefly described in Example 1, above, a KCM pancreatic cancer model was used to assess the effectiveness of a CCR4 inhibitor in combination with an anti-CTLA-4 antibody. The study design is shown in FIG. 1. The mice were broken into 4 groups (n=12 each group): isotype antibody+Vehicle; Isotype Antibody+Compound 1; anti-CTLA-4+Vehicle; anti-CTLA-4+Compound 1. The mice used were 7-8 week old C57BL/6 female mice. Anti-CTLA-4 (BioXcell: anti-mouse CTLA-4 (Clone: 9H10), raised in Syrian Hamster, purified with protein G) and isotype matched control antibody were injected i.p. at 100 µg/mice on day 7, 11, and 16. Compound 1 (40 mg/kg) and vehicle dose p.i. twice daily (bid). KCM cells in matrigel were injected into the pancreas.

After completion of the study, the tumor/pancreases weight for each group was measured. The results are shown in FIG. A-C. As displayed in this figure, Compound 1 alone or in combination with anti-CTLA-4 reduced tumor burden in the KCM tumor model. In this model, most mice develop a secondary tumor on the abdominal wall near the incision sites. These secondary tumors were dissected and the weights were included in the total tumor plus pancreas weights. Primary tumors were weighed together with pancreas as they cannot be surgically separated. Spleen weights were also reduced by Compound 1 treatment. Adequate compound levels were confirmed by measuring plasma compound concentrations at trough on day 12.

Changes in suppressive immune cell populations were also measured at the completion of this study. On day 25 after KCM cell inoculation, primary tumor (together with pancreas) and secondary tumor were dissected, minced and digested with collagenase D for immune cell analysis by flow cytometry. Pancreas from sham-operated mice were processed and analyzed. Results looking at changes in T-regulatory cells, G-MDSC, and M-MDSC from the process material are shown in FIG. 3A-F. These cell populations are shown as cell number per gram of tissue (Panels A-C) or as percentage of CD45+ cells (Panels D-F). While no changes were observed on T regulatory (CD4+/FoxP3+) cells, both monocytic and granulocytic myeloid-derived suppressor cells (mMDSC—CD11b+/Ly6G–/Ly6C-high, gMDSC-CD11b+/Ly6G+/Ly6C-low) showed a trend of decrease with a-CTLA-4/Compound 1 treatment vs. a-CTLA-4 treatment alone.

Example 4: Combination Therapy Using a CT26 Colon Cancer Model

Figure 4:
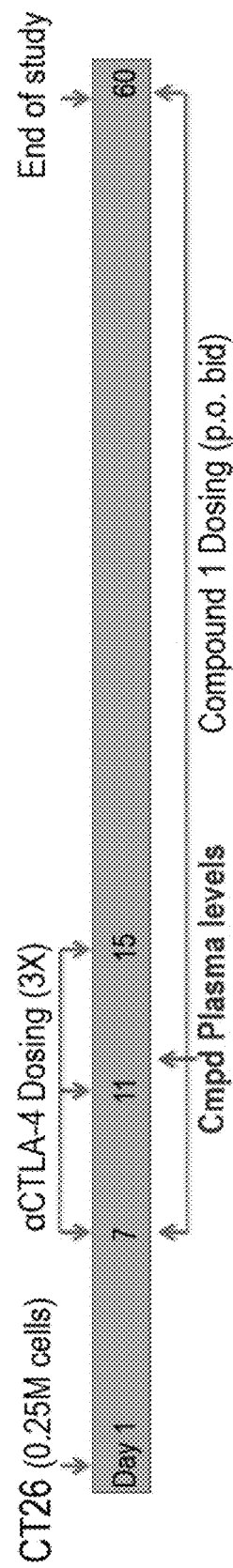
FIG. 4 illustrates the study design used for the CT26 colon cancer tumor model.

As briefly described in Example 1, above, a CT26 colon cancer model was used to asses the effectiveness of a CCR4 inhibitor in combination with an anti-CTLA-4 antibody. The study design is shown in FIG. 4. The mice were broken into 4 groups (n=12 each group): isotype antibody+Vehicle; Isotype Antibody+Compound 1; anti-CTLA-4+Vehicle; anti-CTLA-4+Compound 1. The mice used were 7-8 week old C57BL/6 female mice. Anti-CTLA-4 (BioXcell: anti-mouse CTLA-4 (Clone: 9H10), raised in Syrian Hamster, purified with protein G) and isotype matched control antibody were injected i.p. at 100 µg/mice on day 7, 11, and 16. Compound 1 (40 mg/kg) and vehicle dose p.i. twice daily (bid). At the beginning of the study, CT25 cells were injected subcutaneously (s.c.).

Figure 5:
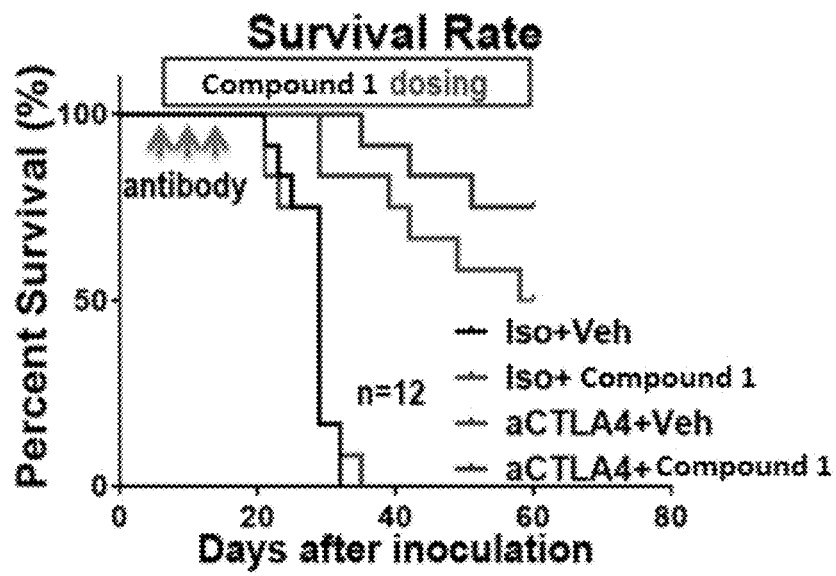
FIG. 5 plots the survival rate of mice during the study from each cohort tested in the CT26 tumor model.
Figure 6:
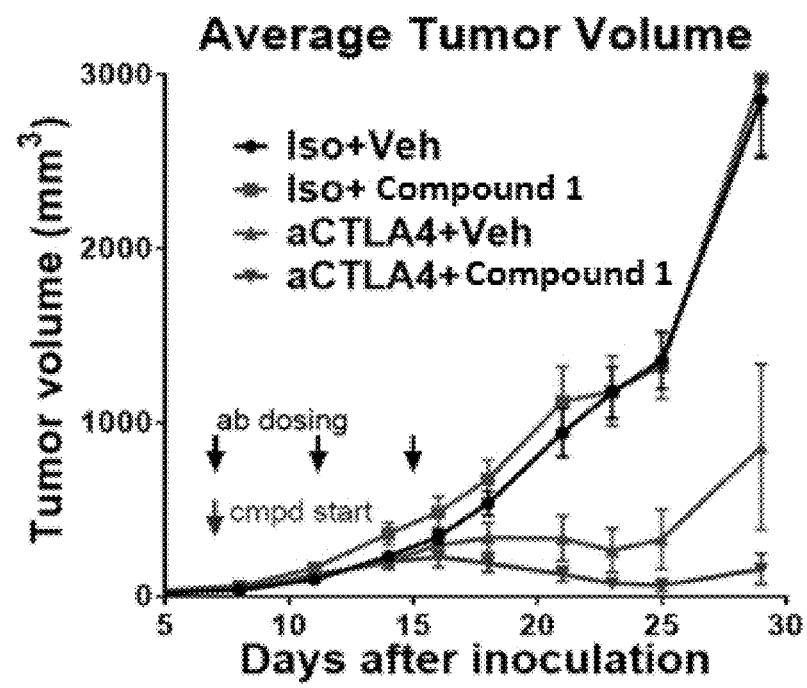
FIG. 6 plots the average tumor volume in mice from each cohort tested
Figure 7A:
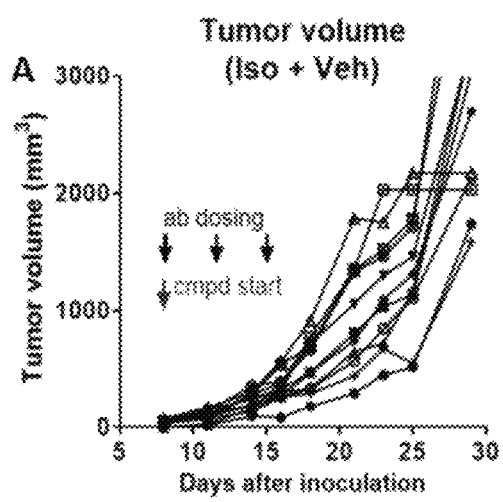
FIG. 7A-D plots the individual tumor volume in mice from each cohort tested. Panel A reports the antibody isotype & vehicle group; Panel B reports the antibody isotype and Compound 1 group; Panel C reports the anti-CTLA-4 antibody and vehicle group; and Panel D reports the anti-CTLA-4 antibody and Compound 1 Group.
Figure 7B:
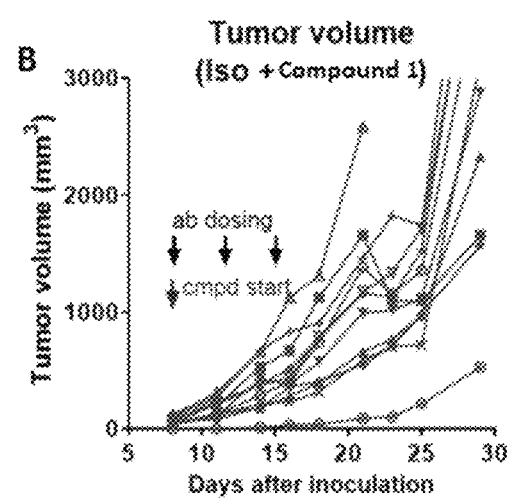
Figure 7C:
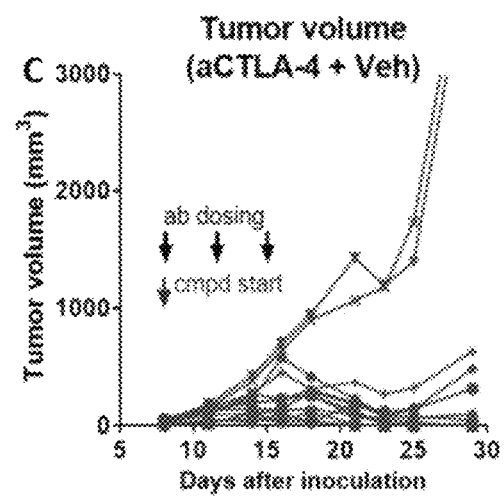
Figure 7D:
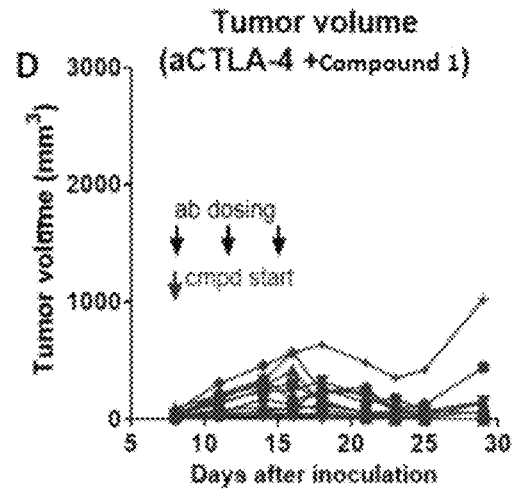
Figure 8A:
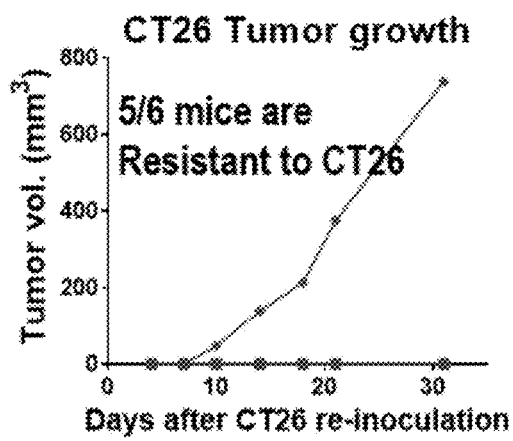
FIG. 8A-F plots tumor volume in re-challenged and naïve mice using CT26 colon cancer cells and 4T1 breast cancer cells. Re-challenged mice are those with complete tumor regression previously treated with anti-CTLA-4 (6 mice) or anti-CTLA-4 and Compound 1 (8 mice). Naïve mice are those who have been previously challenged with CT26 colon cancer cells before. Panel A shows that 5/6 mice from the anti-CTLA-4 treatment group were resistant to CT26 tumor re-introduction; Panel B shows that none of the mice from the anti-CTLA-4 treatment group were resistant to 4T1 tumor cells; Panel C shows that 8/8 mice from the anti-CTLA-4/Compound 1 treatment group were resistant to CT26 tumor re-introduction; Panel D shows that 2 of the 8 mice from the anti-CTLA-4/Compound 1 treatment group were resistant to 4T1 tumor cells; Panel E shows that all naïve mice showed tumor growth when first challenged with CT26 cells; and Panel F shows that none of the naïve mice were resistant to 4T1 tumor cells.
Figure 8B:
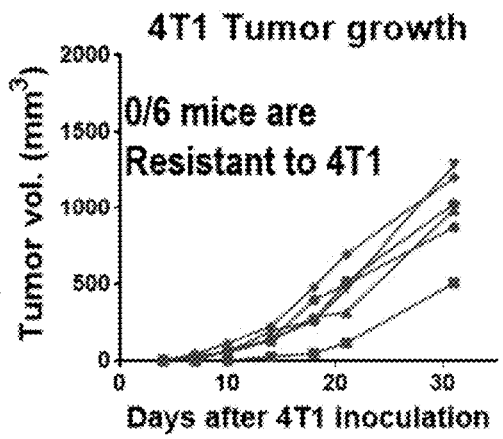
Figure 8C:
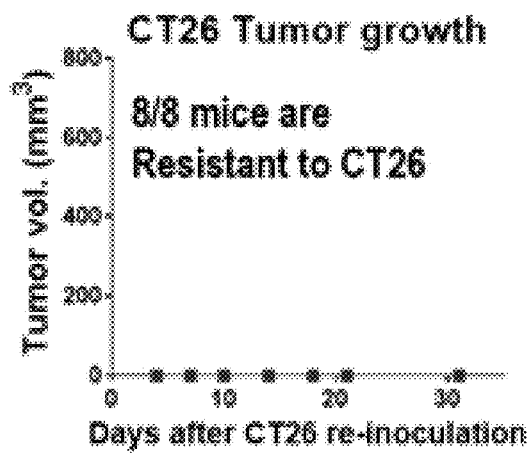
Figure 8D:
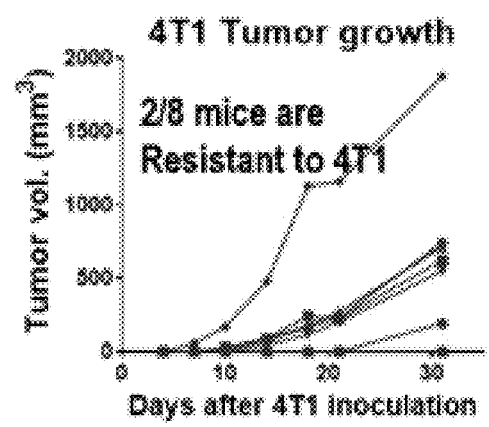
Figure 8E:
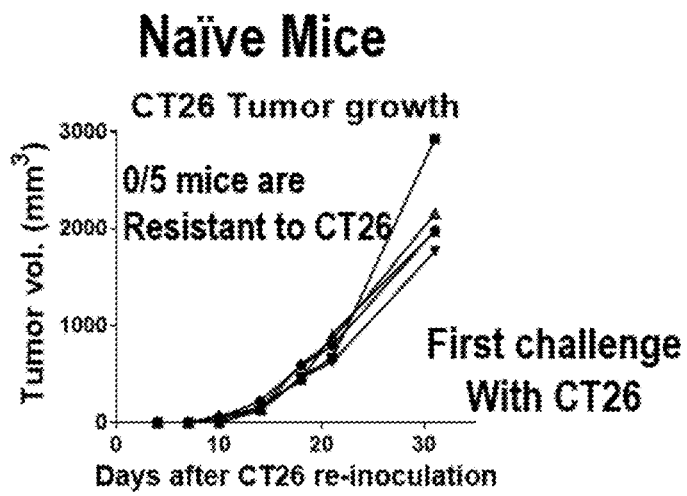
Figure 8F:
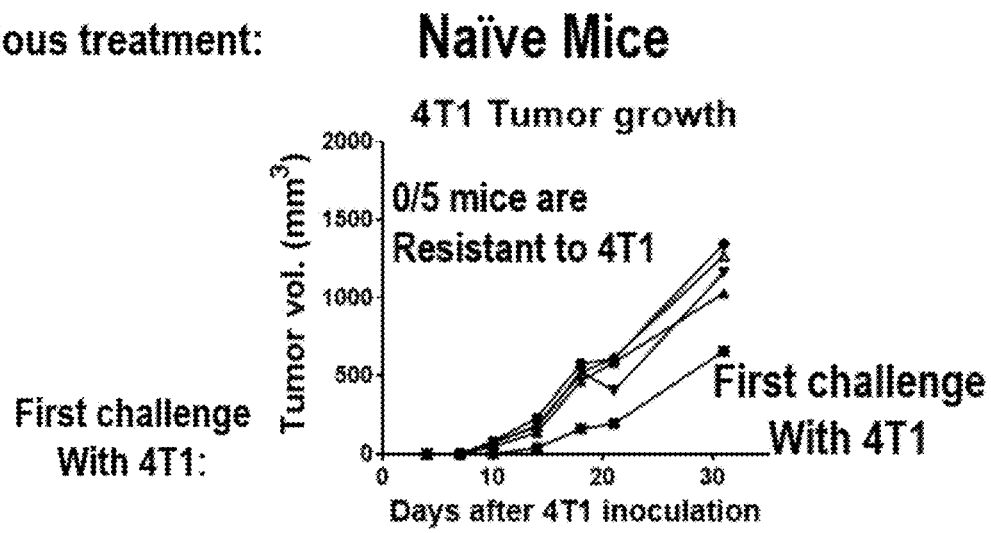

Tumor volume and percent survival were monitored throughout the study. The survival rate is plotted in FIG. 5, and the average tumor volume is plotted in FIG. 6. As seen in FIG. 6, the combination of Compound 1 with an anti-CTLA-4 reduced tumor growth and improved survivial. Individual tumor sizes of each treatment group are shown in FIG. 7A-D. Note how particular mice in the aCTLA-4+Vehicle group (Panel C) have tumors that are completely unresponsive to aCTLA-4 treatment, while the combination on aCTLA+Compound 1 shows that all tumors are responsive to treatment (Panel D).

Three months after the last dosing, mice with complete tumor regression previously treated with a-CTLA-4 (6 mice) or a-CTLA-4/Compound 1 (8 mice) were re-challenged with CT26 tumor cells s.c. on left flank, and these mice were also injected with 4T1 mouse breast cancer cells s.c on the right flank. The results are shown in FIG. 8A-F. As seen in this figure, 1 of 6 mice previously treated with a-CTLA-4 (Panel A), while none of the 8 mice previously treated with a-CTLA-4/Compound 1, developed CT26 tumors (Panel B). All 6 mice previously treated with a-CTLA-4 developed 4T1 tumors (Panel D), while 2 of 8 previously treated with a-CTLA-4/Compound 1 did not develop 4T1 tumors (Panel E). All 5 naïve mice developed both CT26 and 4T1 tumors (Panels C and F).

Blood cells from mice in FIG. 8 were stained with fluorescence-labeled AH1 peptide, both before and 7 days after CT26 re-challenge. AH1 is the immunodominant peptide for cytotoxic T cell response against CT26 tumor cells, and it labels CT26 antigen-reactive CD8+ T cells. Flow cytometry analysis of these samples are shown in FIG. 9A-C. These CT26 antigen-reactive CD8+ T cells are largely absent from the peripheral blood of naive mice, but are abundant in majority of surviving CT26 mice even 3 months after last dosing (Panel A and B). Re-challenge with CT26 cells further increased the number of these cells in the surviving mice from previous treatments, but had minimal effects in naïve mice (Panel C).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A method of treating colon cancer in a human, said method comprising administering an effective amount of a small molecule C-C Chemokine Receptor 4 (CCR4) inhibitor and an anti-CTLA-4 antibody, wherein the CCR4 inhibitor has the following formula (If)

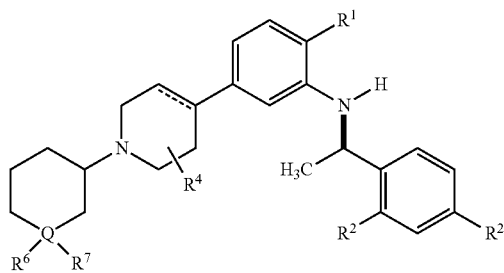

or a pharmaceutically acceptable salt thereof, wherein
$R^1$ is halogen;
each $R^2$ is halogen;
$R^4$ is hydrogen;
Q is N;
$R^6$ is alkylene-C(O)$OR^a$;
 wherein
  $R^a$ is hydrogen; and
$R^7$ is absent.

2. The method of claim 1, wherein said CCR4 inhibitor has the formula (Compound 1)

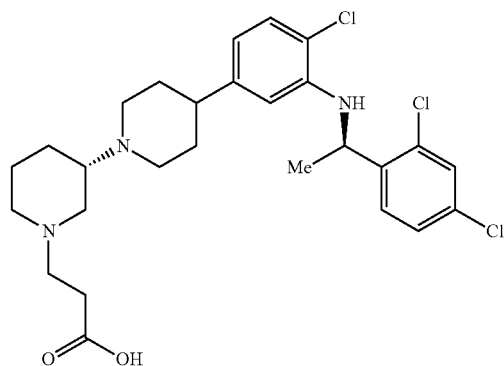

or a pharmaceutically acceptable salt thereof.

3. The method of claim 1, wherein said CCR4 inhibitor has the formula (Compound 2)

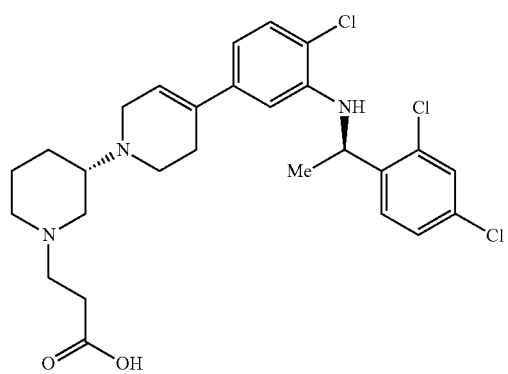

or a pharmaceutically acceptable salt thereof.

4. The method of claim 1, wherein said CCR4 inhibitor has the formula (Compound 3)

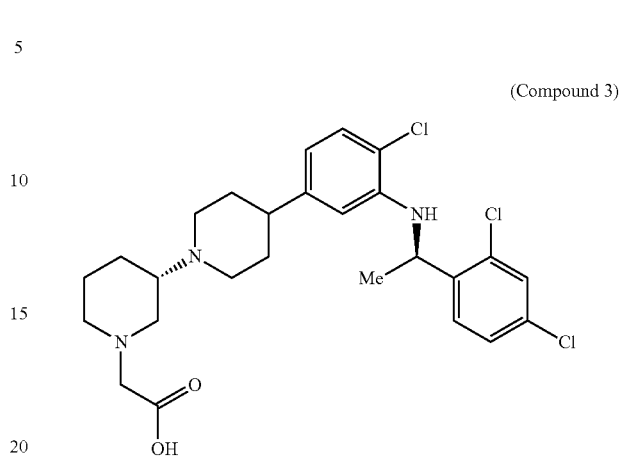

or a pharmaceutically acceptable salt thereof.

5. The method of claim 1, wherein said CCR4 inhibitor has the formula (Compound 4)

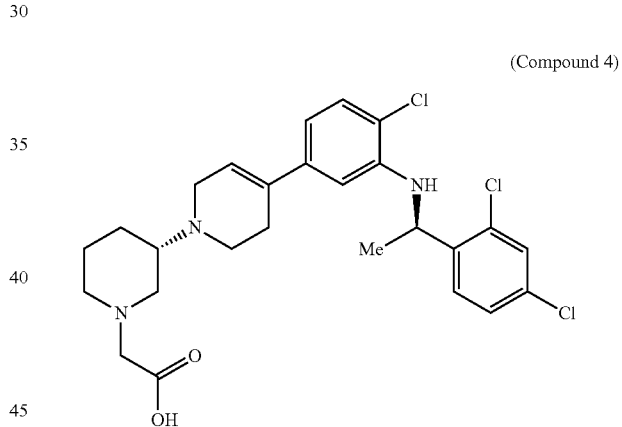

or a pharmaceutically acceptable salt thereof.

6. The method of claim 1, wherein the anti-CTLA-4 antibody is selected from the group consisting of Ipilimumab, Tremelimumab, AGEN1884, and AGEN2041.

7. The method of claim 1, wherein said anti-CTLA-4 antibody is Ipilimumab.

8. The method of claim 1, wherein said anti-CTLA-4 antibody is Tremelimumab.

9. The method of claim 1, wherein said anti-CTLA-4 antibody is AGEN1884.

10. The method of claim 1, wherein said anti-CTLA-4 antibody is AGEN2041.

* * * * *